United States Patent
Arnold et al.

(10) Patent No.: US 8,299,061 B2
(45) Date of Patent: Oct. 30, 2012

(54) INHIBITORS OF DIACYLGLYCEROL ACYLTRANSFERASE

(75) Inventors: Macklin Brian Arnold, Morgantown, IN (US); Thomas James Beauchamp, Fishers, IN (US); Emily Jane Canada, Indianapolis, IN (US); Erik James Hembre, Indianapolis, IN (US); Jianliang Lu, Fishers, IN (US); John Robert Rizzo, Brownsburg, IN (US); John Mehnert Schaus, Zionsville, IN (US); Qing Shi, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 92 days.

(21) Appl. No.: 12/961,714

(22) Filed: Dec. 7, 2010

(65) Prior Publication Data

US 2011/0144091 A1    Jun. 16, 2011

Related U.S. Application Data

(60) Provisional application No. 61/285,317, filed on Dec. 10, 2009.

(51) Int. Cl.
  *A01N 43/00* (2006.01)
  *A61K 31/55* (2006.01)
  *C07D 403/00* (2006.01)
  *C07D 235/02* (2006.01)

(52) U.S. Cl. ............ 514/214.02; 540/603; 548/302.1

(58) Field of Classification Search .......... 540/603; 548/302.1; 514/214.02
  See application file for complete search history.

(56) References Cited

U.S. PATENT DOCUMENTS

| | | | |
|---|---|---|---|
| 4,735,941 | A | 4/1988 | Freidinger et al. |
| 4,847,248 | A | 7/1989 | Freidinger et al. |
| 5,439,906 | A | 8/1995 | Bock et al. |
| 5,679,672 | A | 10/1997 | Baldwin et al. |
| 5,696,111 | A | 12/1997 | Baldwin et al. |
| 5,834,464 | A | 11/1998 | Bock et al. |
| 7,105,509 | B2 | 9/2006 | Pineiro et al. |
| 2008/0090876 | A1 | 4/2008 | Cheng et al. |

FOREIGN PATENT DOCUMENTS

| | | |
|---|---|---|
| EP | 0272866 | 12/1987 |
| EP | 0523846 | 6/1992 |
| JP | 2010116364 | 5/2010 |
| WO | 9514671 | 6/1995 |
| WO | 9828268 | 7/1998 |
| WO | 2006020959 | 2/2006 |
| WO | 2007016087 | 2/2007 |
| WO | 2009126624 | 10/2009 |
| WO | 2009126861 | 10/2009 |
| WO | 2010056496 | 5/2010 |
| WO | 2010084979 | 7/2010 |
| WO | 2010095766 | 8/2010 |

*Primary Examiner* — Sreeni Padmanabhan
*Assistant Examiner* — Sarah Pihonak
(74) *Attorney, Agent, or Firm* — John C. Demeter; MaCharri Vorndran-Jones

(57) ABSTRACT

This invention provides compounds of formula I:

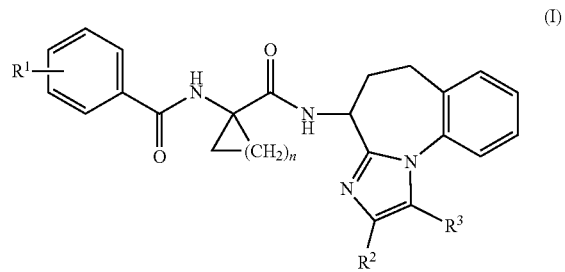

or a pharmaceutically acceptable salt thereof; as well as a method for treating obesity, a method for treating diabetes, and a pharmaceutical composition.

16 Claims, No Drawings

INHIBITORS OF DIACYLGLYCEROL ACYLTRANSFERASE

This invention provides compounds that inhibit diacylglycerol acyltransferase 1 (DGAT-1).

It has been proposed that inhibition of DGAT-1, a key enzyme in triglyceride synthesis may provide a novel approach to treating obesity and/or improving insulin sensitivity. Although DGAT is reported to be an excellent target for a small molecule inhibitor, only a limited number of compounds have been reported to inhibit DGAT-1 activity. No known DGAT-1 inhibitors are approved for pharmaceutical use. Hence, there is a need for more small molecules that inhibit DGAT-1. There is a particular need for DGAT-1 inhibitor compounds having a desirable pharmacological profile.

Compounds reported to be modulators of DGAT are disclosed in US 2008/0090876 (Cheng et. al.). The compounds disclosed by Cheng are thianecarboxamides. Cycloalkyl, lactam, lactone, and related compounds are reported in WO98/28268 (We et. al.) as inhibitors of β-amyloid peptide release for use in the treatment of Alzheimer's Disease. Acylbenzazepines are disclosed in U.S. Pat. No. 5,696,111 (Balwin et. al.) as compounds that may be used to treat arrhythmias. In contrast, the presently claimed imidazo-benzazepines, are structurally diverse from those of Cheng, We, and Balwin. Further, there is no teaching or suggestion that the compounds of We or Balwin could be used as DGAT-1 inhibitors. Azepinone compounds are reported to be modulators of DGAT in WO 2010/056496, published 20 May 2010. The azepinone compounds reported in WO 2010/056496 are structurally diverse from the presently claimed imidazo-benzazepines.

Compounds of this invention are potent inhibitors of DGAT-1. This invention provides a desired novel treatment option acting through a pharmacological mechanism that is unique compared to commercially available treatments. Further, certain compounds of this invention selectively inhibit DGAT-1 as compared to DGAT-2. The pharmacological profile of compounds of this invention, as selective DGAT-1 inhibitors, can be particularly desirable for use in the treatment of obesity and/or improving insulin sensitivity.

This invention provides compounds of formula I:

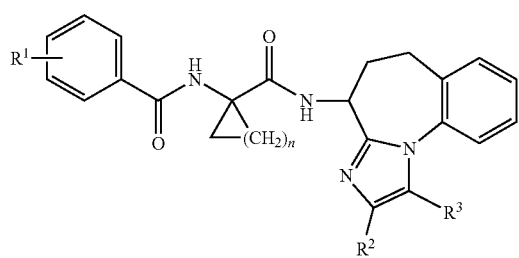

(I)

or a pharmaceutically acceptable salt thereof;
wherein
$R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —O$CF_3$;
$R^2$ is selected from the group consisting of H and —$CH_3$;
$R^3$ is selected from the group consisting of H and —$CH_3$; provided that at least one of the group consisting of $R^2$ and $R^3$ is H; and
n is 1, 2, or 3.

Preferably, this invention provides compounds of formula I wherein
$R^1$ is selected from the group consisting of H, F, Cl, —$CF_3$, —$CH_3$, —OH, —$OCH_3$, —$OCH_2CH_3$, —$OCH_2CH_2CH_3$, —$OCH_2CH(CH_3)_2$, —O-cyclopropyl, —O—$CH_2$-phenyl, —OC(H)$F_2$, and —O$CF_3$, n is 1 or 3; and $R^2$ and $R^3$ are each H.

Preferably, this invention provides compounds of formula I or a pharmaceutically acceptable salt thereof;
wherein
$R^1$ is selected from the group consisting of H, F, Cl, —$CF_3$, —$CH_3$, —OH, —$OCH_3$, —$OCH_2CH_3$, —$OCH_2CH_2CH_3$, —$OCH_2CH(CH_3)_2$, —O-cyclopropyl, —O—$CH_2$-phenyl, —OC(H)$F_2$, and —O$CF_3$; and
n is 1.

Preferably, this invention provides compounds of formula I or a pharmaceutically acceptable salt thereof;
wherein
$R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —O$CF_3$; and n is 3.

Preferably, this invention provides compound of the formula I or a pharmaceutically acceptable salt thereof;
wherein $R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —O$CF_3$; n is 3; and $R^3$ is H.

Preferably, this invention provides compound of the formula I or a pharmaceutically acceptable salt thereof;
wherein $R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —O$CF_3$; n is 1; and $R^3$ is H.

The following may be preferred:

Compounds of Formula I or a salt thereof wherein $R^3$ is H are preferred.

Compounds of Formula I or a salt thereof wherein n is 1 or 3 are preferred.

Compounds of Formula I or a salt thereof wherein n is 1 are preferred.

Compounds of Formula I or a salt thereof wherein $R^2$ is H and $R^3$ is H are also preferred.

Compounds of Formula I or a salt thereof wherein the compound is the R isomer are preferred.

Compounds of Formula I or a salt thereof wherein $R^1$ is selected from the group consisting of F, Cl, —$CF_3$, —$CH_3$, —OH, —$OCH_3$, —$OCH_2CH_3$, —$OCH_2CH_2CH_3$, —$OCH_2CH(CH_3)_2$, —O-cyclopropyl, —O—$CH_2$-phenyl, —OC(H)$F_2$, and —O$CF_3$ are preferred.

Compounds of Formula I or a salt thereof wherein $R^1$ is selected from the group consisting of F, Cl, and —O($C_1$-$C_4$ alkyl) are preferred.

Compounds of Formula I or a salt thereof, wherein $R^1$ is selected from the group consisting of Cl and —O($C_1$-$C_4$ alkyl) are preferred.

Compounds of Formula I or a salt thereof wherein $R^1$ is —$OCH_2CH_3$ is preferred.

Compounds of Formula I or a salt thereof wherein $R^1$ is Cl are preferred.

Compounds of Formula I or a salt thereof wherein $R^2$ is $CH_3$, and $R^3$ is H are also preferred.

Compounds wherein n is 3 are preferred.

A preferred embodiment is a compound of the formula:

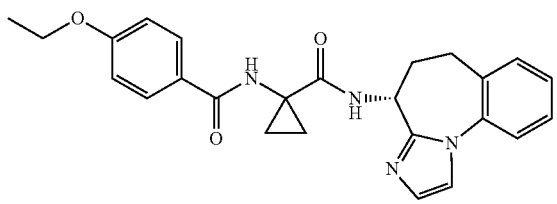

or a pharmaceutically acceptable salt thereof
A preferred embodiment is a compound of the formula:

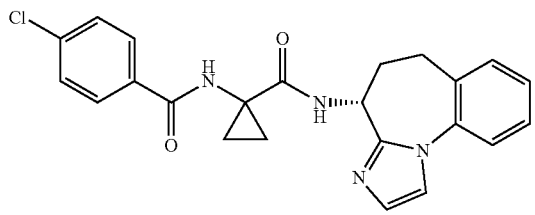

or a pharmaceutically acceptable salt thereof.

The compounds of formula I may be in the form of a racemic mixture. The preferred isomer is the "R" stereo form, illustrated herein below as Formula II.

Preferably, this invention provides compounds of formula I having the following isomeric conformation, illustrated as formula II:

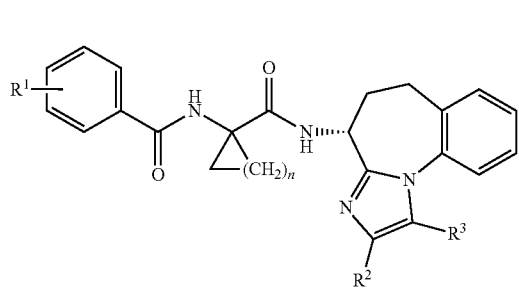

(II)

or a pharmaceutically acceptable salt thereof.

Compounds of formula I may be synthesized and the R and the S isomers may then separated by chiral chromatography. Compounds of formula I may be synthesized using chiral synthesis to specifically synthesize the preferred R isomer.

A further embodiment of this invention provides the use of a compound as claimed by the present invention or a pharmaceutically acceptable salt thereof in the manufacture of a medicament for the treatment of diabetes and/or obesity. Another embodiment of the invention is a compound as claimed by the present invention, or a salt thereof, for use in treating obesity. A further embodiment of this invention is a compound as claimed herein or a pharmaceutically acceptable salt thereof for use in therapy. A further embodiment of the invention is a compound as claimed by the present invention, or a pharmaceutically acceptable salt thereof for use in the treatment of diabetes. Further, the invention relates to a compound as claimed by the present invention for use in improving insulin sensitivity in a mammal.

This invention provides a method for treating obesity in a mammal, comprising the step of administering to the mammal a compound as claimed by the present invention or a pharmaceutically acceptable salt thereof. This invention provides a method for treating diabetes and/or improving insulin sensitivity in a mammal, comprising the step of administering to the mammal a compound as claimed by the present invention or a pharmaceutically acceptable salt thereof. A further embodiment of this invention is a method for treating dyslipidemia in a mammal comprising the step of administering to the mammal a compound as claimed by the present invention or a pharmaceutically acceptable salt thereof. A further embodiment of this invention is a method for treating acne in a mammal comprising the step of administering to the mammal a compound as claimed by the present invention or a pharmaceutically acceptable salt thereof. A further embodiment of this invention is a method for treating hepatitis C virus (HCV) infection comprising the step of administering to the mammal a compound as claimed by the present invention or a pharmaceutically acceptable salt thereof.

In another embodiment, the present invention also relates to pharmaceutical compositions comprising a compound as claimed by the present invention, or a pharmaceutically acceptable salt thereof, and a pharmaceutically acceptable carrier. A further embodiment is a pharmaceutical composition of the present invention further comprising a second pharmaceutical agent.

In another embodiment, the present invention relates to formulations comprising a compound as claimed by the present invention, or a pharmaceutically acceptable salt thereof, a pharmaceutically acceptable carrier, and hydroxypropyl methylcellulose. A further embodiment is a pharmaceutical formulation wherein the hydroxyproyl methylcellulose is hydroxypropyl methylcellulose acetate succinate (HPMC-AS-L). A further embodiment is a process for preparing a formulation comprising contacting a compound as claimed by the present invention, or a pharmaceutically acceptable salt thereof, with hydroxypropylmethyl cellulose. A further embodiment is a process for preparing a pharmaceutical formulation wherein the hydroxymethyl cellulose is hydroxypropyl methylcellulose acetate succinate (HPMC-AS-L).

"Pharmaceutically-acceptable salt" refers to salts of the compounds of the invention considered to be acceptable for clinical and/or veterinary use. These salts may be prepared by methods known to the skilled artisan. Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," Journal of Pharmaceutical Sciences, Vol. 66, No. 1, January 1977. The compounds of the present invention are preferably prepared as pharmaceutical compositions administered by a variety of routes. The term "pharmaceutically acceptable carrier" means that the carrier, diluent, excipients and salt are pharmaceutically compatible with the other ingredients of the composition. Most preferably, these compositions are for oral administration. Pharmaceutically acceptable compositions and processes for preparing same are well known in the art. See, e.g., REMINGTON: THE SCIENCE AND PRACTICE OF PHARMACY (A. Gennaro, et al., eds., 19 th ed., Mack Publishing Co., 1995).

The compounds of the invention can be prepared using the methods illustrated in Schemes A, B, C, D, E, F, G, H, I, and J and as described by the Preparations and Examples. The Preparations and Examples are named using Symyx® Draw Version 3.1.

The terms and abbreviations used in the Schemes, Preparations, Examples and Procedures herein have their normal meanings unless otherwise designated.

The terms and abbreviations used in the instant Schemes, Preparations, Examples and Procedures have their normal meanings unless otherwise designated. For example, as used herein, the following terms have the meanings indicated: N,N-Dimethylformamide (DMF); Methyl tert-butyl ether (MTBE); tetrahydrofuran (THF); simulated moving bed (SMB) chromatography; methanol (MeOH); lithium hydroxide (LiOH); N-methyl-2-pyrrolidone (NMP); copper iodide (CuI); [1,3-Bis(2,6-diisopropylphenyl)imidazol-2-ylidene] (3-chloropyridyl) Pd (II) dichloride:Cu(I) iodide (PEPPSI™); N,N-Dimethylethylamine (DMEA); and 1,3,5, 2,4,6-trioxatriphosphorinane, 2,4,6-tripropyl-2,4,6-trioxide (T3P).

Scheme A

1)

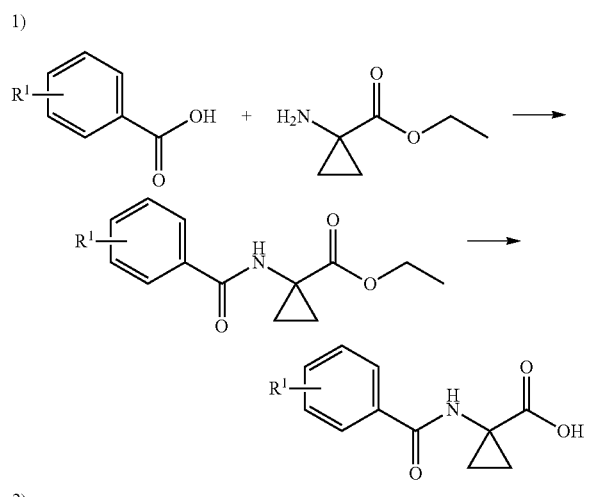

2)

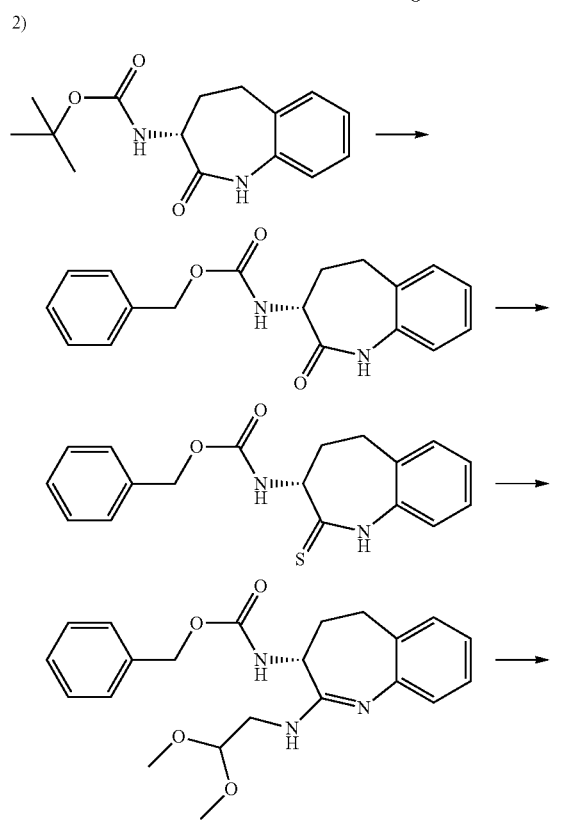

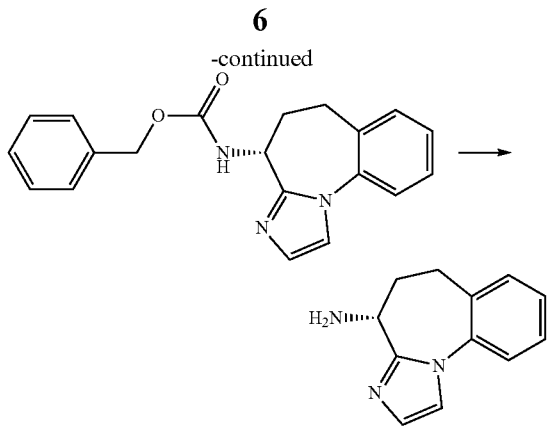

3)

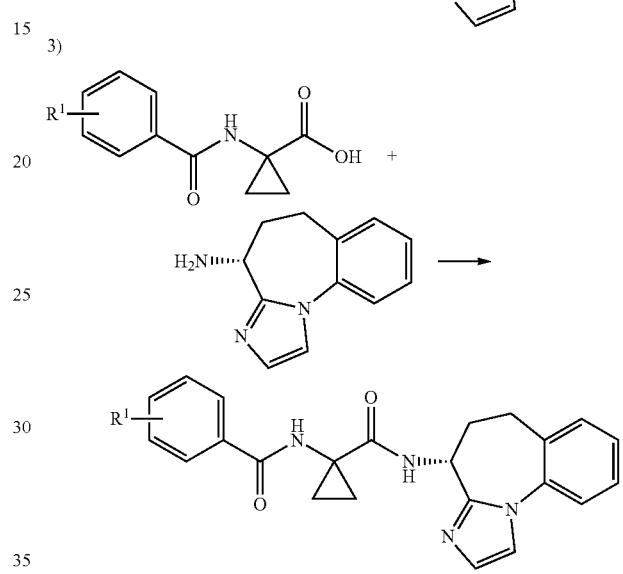

In the above Scheme, preferably, $R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —$OCF_3$. More preferably, $R^1$ is —O($C_1$-$C_4$ alkyl) or Cl. Most preferably, $R^1$ is —$OCH_2CH_3$ or Cl.

Preparation 1

Ethyl 1-[(4-ethoxybenzoyl)amino]cyclopropanecarboxylate

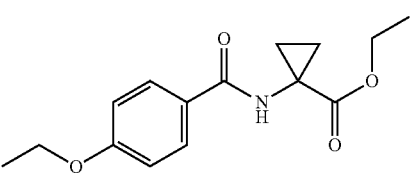

Add oxalyl chloride (189 mL, 2.17 mol) to 4-ethoxybenzoic acid (334.5 g, 1.99 mol) and N,N-dimethylformamide (1 mL) in dichloromethane (3 L). After 1 hr at 25-26° C., concentrate the mixture under reduced pressure until a constant weight is achieved. Stir ethyl 1-aminocyclopropanecarboxylate hydrochloride (300 g, 1.81 mol) and dichloromethane (2.5 L) in an ice water bath. Add triethylamine (631 mL, 4.53 mol) and then add a solution of the acid chloride (ca 380 g) in dichloromethane (500 mL). Stir the reaction mixture for approximately 16 hours at ambient temperature. Dilute the reaction with aqueous 1N hydrochloric acid (1 L). Extract the aqueous layer with dichloromethane (1 L). Wash the organic layer with water (2 L) and brine (2 L). Dry the solution over sodium sulfate, filter, and concentrate under reduced pressure. Slurry the residue in hexanes and filter to give the title compound (478 g, 95%) as an ivory powder: MS (mass spectrometry) (m/z): 278 (M+1).

Preparation 2

1-[(4-ethoxybenzoyl)amino]cyclopropanecarboxylic acid

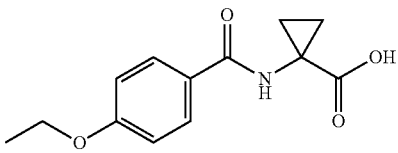

Add ethyl 1-[(4-ethoxybenzoyl)amino]cyclopropanecarboxylate (478 g, 1.72 mol) to tetrahydrofuran (2 L) and methanol (1 L). Dissolve lithium hydroxide (LiOH) (144.7 g, 3.45 mol) in water (1 L) and add it to the mixture. Stir the reaction mixture while heating to 55° C. Cool the reaction to ambient temperature and concentrate under reduced pressure. After removing 2.5 L of solvent, dilute the mixture with water (2 L) and immerse it in an ice water bath. Adjust to pH 2 with aqueous 5N hydrochloric acid (750 mL). Filter the precipitate, wash the cake with water (2×2 L), and dry to give the title compound (425 g, 99%) as a white powder: MS (m/z): 250 (M+1).

Preparation 3

Ethyl 1-[(4-chlorobenzoyl)amino]cyclopropanecarboxylate

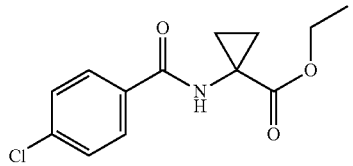

Add ethyl 1-aminocyclopropanecarboxylate (89.2 g, 0.54 mol) to diisopropylethylamine (187.86 mL, 1.08 mol) in dichloromethane (900 mL) Immerse the flask in a cold water bath and slowly add 4-chlorobenzoic acid chloride (75.46 mL, 0.59 moles). After addition is complete, remove the bath, allow the reaction to equilibrate to 20° C., and stir for approximately 2 hours. Wash with 1N hydrochloric acid (HCl), followed by saturated sodium bicarbonate (NaHCO$_3$), water, and then brine. Dry the organic layer over sodium sulfate (Na$_2$SO$_4$), filter, and concentrate under reduced pressure. Slurry the residue with heptane, filter, and rinse with heptane to give the title compound (142 g, 98%) as a white powder: MS (m/z): 268 (M+1).

Preparation 4

1-[(4-Chlorobenzoyl)amino]cyclopropanecarboxylic acid

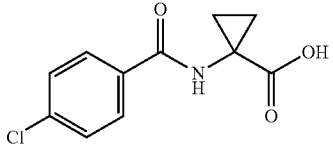

To ethyl 1-[(4-chlorobenzoyl)amino]cyclopropanecarboxylate (157 g, 0.58 mol) in 1,4-dioxane (2.4 L), add a solution of lithium hydroxide (123.05 g, 2.93 mol) in water (1.2 L). Stir the reaction mixture at ambient temperature for 4 hours and then concentrate it under reduced pressure. Dilute the mixture with water (1 L) and immerse it in an ice water bath. Adjust the pH to approximately 2 with aqueous 5N HCl. Filter the precipitate, wash the cake with water (3×1 L), and dry (50° C., vacuum oven) to give (132 g, 94%) the title compound as a white powder: MS (m/z): 240 (M+1).

Preparation 5

Benzyl N-[(3R)-2-oxo-1,3,4,5-tetrahydro-1-benzazepin-3-yl]carbamate

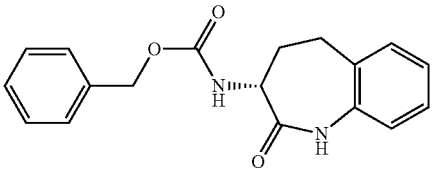

Combine methanol (5000 mL) and 5N aqueous hydrogen chloride solution (1393 mL, 5.57 mol) and heat to 35° C. for 15 minutes. Add tert-butyl N-[(3R)-2-oxo-1,3,4,5-tetrahydro-1-benzazepin-3-yl]carbamate (Armstrong III, Joseph D, et al, Tetrahedron Let. 35(20) pp. 3239-3242 (1994) (770 g, mmol and commercially available) portionwise over 1 hour. Concentrate the mixture under reduced pressure to a white solid. Combine this solid with additional (3R)-3-amino-1,3,4,5-tetrahydro-1-benzazepin-2-one (different lot, same method; 660 g, 3.78 mol) and dissolve in water (2.5 L). To the resulting solution add sodium carbonate (3.17 kg, 3.18 mol) and acetonitrile (7.5 L). Add benzyl chloroformate (7.14 mol, 1.21 Kg) dropwise over 2 hours. After 2 hours at ambient temperature, add ethyl acetate (8 L) and filter. Wash the wet cake with water (4.0 L), acetonitrile (2.0 L), and ethyl acetate (3.0 L). Dry the solid under reduced pressure for 48 hours to give the title compound (2.14 kg, 105%): MS (m/z): 310.8 (M+1).

Preparation 6

Benzyl N-(2-thioxo-1,3,4,5-tetrahydro-1-benzazepin-3-yl)carbamate

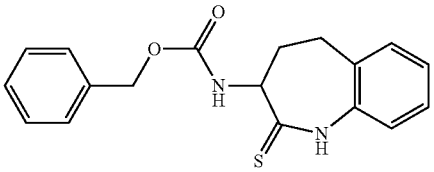

To N-[(3R)-2-oxo-1,3,4,5-tetrahydro-1-benzazepin-3-yl]carbamate (2.13 kg, 6.88 mol) in 2-methyl-tetrahydrofuran (15 L) add phosphorus pentasulfide (1.68 kg, 7.57 mol) over 30 minutes and heat to 50° C. for 24 hours. Cool to 29° C., add silica gel (2.0 Kg), filter, and concentrate under reduced pressure. Dissolve the resulting residue in chloroform (4.0 L) and purify via chromatography (1:1 ethyl acetate:hexanes) to give the title compound (1.65 kg, 73%) as a red solid: MS (m/z): 327 (M+1).

Preparation 7

Benzyl N-[2-(2,2-dimethoxyethylamino)-4,5-dihydro-3H-1-benzazepin-3-yl]carbamate

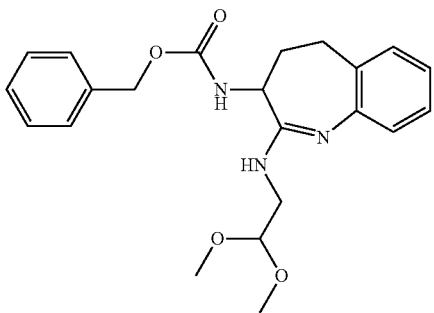

Dissolve Benzyl N-(2-thioxo-1,3,4,5-tetrahydro-1-benzazepin-3-yl)carbamate (1.78 Kg, 5.13 mol) and para-toluene sulfonic acid monohydrate (48.8 g, 256 mmol) in dichloromethane (12 L). Add aminoacetaldehyde dimethyl acetal (2.70 Kg, 25 mole) dropwise over 1 hour and stir for 36 hours at ambient temperature. Add additional aminoacetaldehyde dimethyl acetal (1.40 Kg, 13 mol) and stir for 12 hours at ambient temperature. Add water (5.0 L), separate the organic layer, and extract the aqueous with dichloromethane (2.0 L). Combine the organic layers and wash with water, saturated ammonium chloride (6.0 L), and brine (4.0 L). Filter the organic through diatomaceous earth and concentrate under reduced pressure to give the title compound (2.30 kg, 118%) as a yellow oil: MS (m/z): 398 (M+1).

Preparation 8

Benzyl N-[(4R)-5,6-dihydro-4H-imidazo[1,2-a][1]benzazepin-4-yl]carbamate

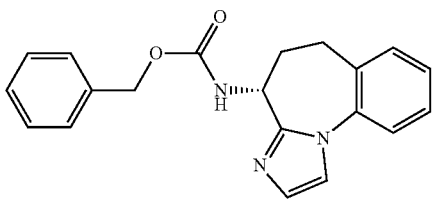

Heat a mixture of benzyl N-[2-(2,2-dimethoxyethylamino)-4,5-dihydro-3H-1-benzazepin-3-yl]carbamate (1.80 kg, 4.1 mol) and formic acid (6.4 L) at 95° C. for 80 minutes. Concentrate the mixture under reduced pressure to give a black oil and partition it between dichloromethane (7.0 L) and water (5 L). Add sodium carbonate until the pH of the aqueous layer is 7. Remove the organic layer and wash with water (3x). Extract the aqueous layers with dichloromethane. Combine the organic layers and concentrate under reduced pressure to give a black oil. Divide the 2.297 kg of the black oil into approximately 250 g sections and dissolve each section in dichloromethane (250 mL). Add to 3.5 kg Merck 9385, 60 A, 230-400 mesh silica. Elute target compound with 75:25 ethyl acetate/heptane beginning with six column volumes (faster eluting impurities elute first). Follow with 5:95 methanol/ethyl acetate to remove remaining product (1082 g recovered). Assay product mixture using chiral HPLC conditions as follows: 4.6×150 mm Chiralpak AD-H column, 15:85:0.2 acetonitrile/3A grade ethanol/dimethylethylamine mobile phase, 0.6 mL/min flow rate, 250 nm UV detection. Observe isomer ratio 3:2 desired/undesired under these conditions. Dissolve isomer mixture at 30 mg/mL 20:80 acetonitrile/3A ethanol. Purify isomers using prep chiral HPLC conditions as follows: 8×40.5 cm Chiralpak AD (20 micron) column, 20:80:0.2 acetonitrile/3A ethanol/N,N-dimethylethylamine (DMEA) mobile phase, 490 mL/min flow rate, 250 nm UV detection, 1.5 g (50 mL) injections, 4.6 minute cycle time/injection using Steady State Recycle (SSR) technology (J. H. Kennedy, M. D. Belvo, V. S. Sharp, J. D. Williams, Comparison of separation efficiency of early phase active pharmaceutical intermediates by steady state recycle and batch chromatographic techniques, Journal of Chromatography A, 1046 p 55-60 (2004)). The collection of isomer 1 is from 0.4-0.9 min and collection of isomer 2 is from 2.4-4.2 min. The desired isomer (Isomer 2; R isomer) is the second eluter: benzyl N-[(4R)-5,6-dihydro-4H-imidazo[1,2-a][1]benzazepin-4-yl]carbamate. Concentrate the product containing fractions under reduced pressure to give the title compound (615 g, 73%) as a white solid: MS (m/z): 334 (M+1).

Preparation 9

(4R)-5,6-Dihydro-4H-imidazo[1,2-a][1]benzazepin-4-amine dihydroiodide

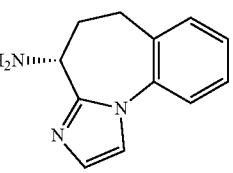

Add iodotrimethylsilane (783 mL, 5.49 mol) to dichloromethane (800 mL) and cool in an ice water bath. Dissolve benzyl N-[(4R)-5,6-dihydro-4H-imidazo[1,2-a][1]benzazepin-4-yl]carbamate (610 g, 1.83 mol) in dichloromethane (1 L) and add to the iodotrimethylsilane solution. After addition is complete, remove the ice water bath and allow the reaction to stir for approximately 16 hours at ambient temperature. Stir a mixture of hexanes (6 L) and ethanol (1 L) in an ice water bath. Add the reaction mixture to the stirring hexane/ethanol mixture carefully to avoid foaming. Stir it at ambient temperature 10 minutes. Remove the resulting solid by filtration and wash the cake with hexanes (3×2 L) to give the title compound (817.1 g, 98%) as an orange, free flowing solid: MS (m/z): 200 (M+1).

Preparation 10

(4R)-5,6-Dihydro-4H-imidazo[1,2-a][1]benzazepin-4-amine

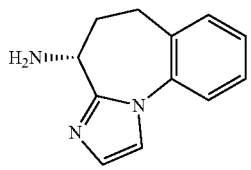

Combine benzyl N-[(4R)-5,6-dihydro-4H-imidazo[1,2-a][1]benzazepin-4-yl]carbamate (120.0 g, 359.9 mmol) and ethanol (2.0 L) in a Büchi hydrogenator and add 10% palladium on carbon (Pd/C) (10.0 g, 9.4 mmol) slurried in toluene (200 ml). Hydrogenate (60 psi, ambient temperature) the mixture for approximately 64 hours. Filter the mixture through diatomaceous earth and wash the cake with THF (300 ml). Concentrate the filtrate under reduced pressure to give the title compound (60 g, 84%) as a white foam: MS (m/z): 200 (M+1).

EXAMPLE 1

N-[1-[[(4R)-5,6-dihydro-4H-imidazo[1,2-a][1]benzazepin-4-yl]carbamoyl]cyclopropyl]-4-ethoxy-benzamide

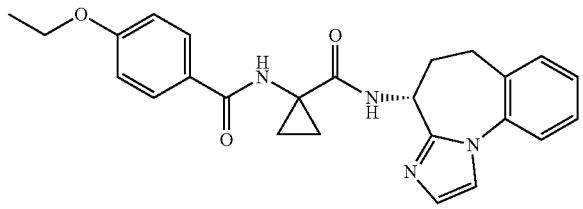

Add (4R)-5,6-dihydro-4H-imidazo[1,2-a][1]benzazepin-4-amine dihydroiodide (650 g, 1.43 mol), 1-[(4-ethoxybenzoyl)amino]cyclopropanecarboxylic acid (427 g, 1.71 mol), and 1-hydroxybenzotriazole hydrate (262.5 g. 1.71 mol) to dichloromethane (3 L). Stir the mixture in an ice water bath and slowly add diisopropylethylamine (797 ml, 4.57 mol). Add 1-(3-dimethylaminopropyl)-3-ethylcarbodiimide hydrochloride (333.6 g, 1.71 mol) over 10 minutes. Remove the ice water bath and allow the mixture to stir for approximately 16 hours at ambient temperature. Wash the reaction mixture with water (3×4 L). Dry the organic phase over sodium sulfate. Filter and concentrate the mixture under reduced pressure to approximately 1 L volume. Dilute the residue with ethyl acetate (4 L). Remove 2 L of solvent under reduced pressure. Allow mixture to stand 1 hour at ambient temperature. Isolate the resulting precipitate by filtration and wash the cake with hexanes (2×2 L) to give the title compound (569.9 g, 93%) as a pale tan solid: MS (m/z): 431 (M+1). $H^1$ NMR (399.81 MHz, DMSO): 8.91 (s, 1H), 7.95-7.93 (d, J=7.5 Hz, 1H), 7.87-7.83 (d, J=8.7 Hz, 2H), 7.49 (d, J=1.4 Hz, 1H), 7.44-7.43 (d, J=7.6 Hz, 1H), 7.38 (m, 2H), 7.34-7.29 (m, 1H), 7.00-6.96 (d, J=8.7 Hz, 2H), 6.95 (d, J=1.3 Hz, 1H), 4.65-4.60 (m, 1H), 4.08 (q, J=7.0 Hz, 2H), 2.70-2.65 (m, 1H), 2.59-2.56 (m, 1H), 2.33-2.28 (m, 1H), 2.04-2.00 (m, 1H), 1.34-1.31 (m, 4H), 1.27-1.25 (m, 1H), 1.03-0.98 (m, 1H), 0.96-0.90 (m, 1H).

EXAMPLE 2

4-Chloro-N-[1-[[(4R)-5,6-dihydro-4H-imidazo[1,2-a][1]benzazepin-4-yl]carbamoyl]cyclopropyl]benzamide

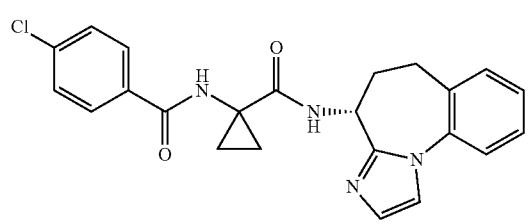

Add 1-(3-dimethylaminopropyl)-3-ethylcarbodiimide hydrochloride (29 g, 151 mmol) to a 10° C. slurry of (4R)-5,6-dihydro-4H-imidazo[1,2-a][1]benzazepin-4-amine (30 g, 151 mmol), 1-hydroxybenzotriazole (20 g, 151 mmol), triethylamine (41.97 mL, 301 mmol), and 1-[(4-chlorobenzoyl)amino]cyclopropanecarboxylic acid (40 g, 166 mmol) in THF (300 mL). Remove the ice bath, warm the mixture to ambient temperature, and stir it for 4 hours. Pour the mixture into water (1.0 L) and extract with ethyl acetate (1.0 L). Wash the organic phase with saturated sodium bicarbonate (500 mL), dry over magnesium sulfate, filter, and concentrate under reduced pressure. Slurry the residue in ethyl acetate (300 mL) and heat to 71° C. Cool to ambient temperature, filter the precipitate, and wash with ethyl acetate (100 mL) to give the title compound (38.8 g, 61%): MS (m/z): 421 (M+1).

Scheme B

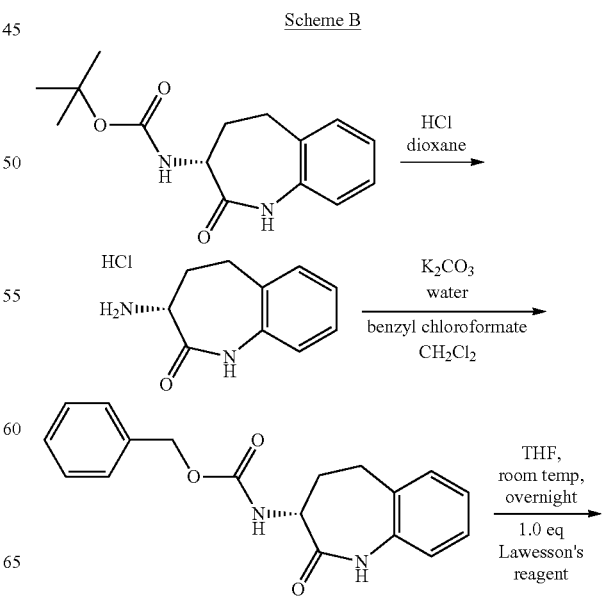

-continued

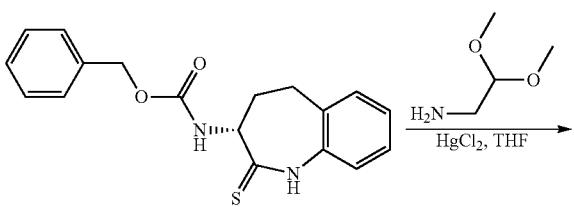

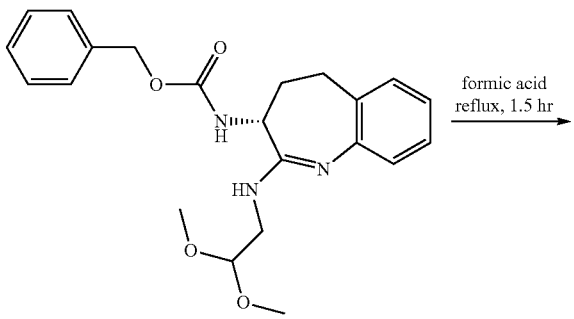

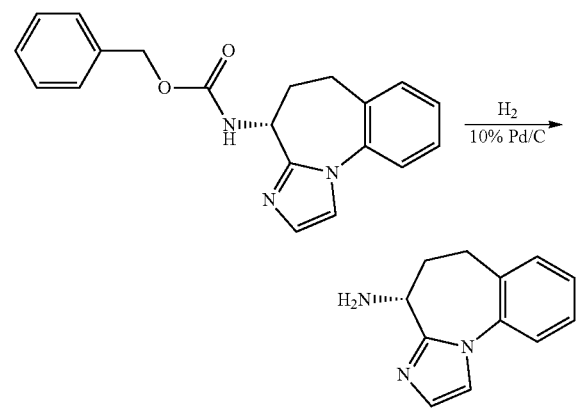

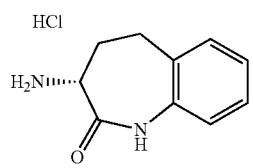

In Scheme B, the chiral synthetic procedure results in the "R" isomer.

Preparation 11

(3R)-3-Amino-1,3,4,5-tetrahydro-1-benzazepin-2-one hydrochloride

Slurry tert-butyl N-[(3R)-2-oxo-1,3,4,5-tetrahydro-1-benzazepin-3-yl]carbamate, (prepare essentially by the method described in Armstrong III, Joseph D, et al, Tetrahedron Let. 35(20) pp. 3239-3242 (1994), 15 g, 54.28 mmol) in 1,4-dioxane (100 mL, 1.17 moles) and cool it in an ice bath. Rapidly add HCl in dioxane (100 mL, 4.0 M) and remove the bath after the addition. After 3 hours add more HCl in dioxane (100 mL, 4.0 M). Stir the reaction for approximately 16 hours. Collect the solid by filtration, wash it with a small volume of ether, and dry it in an oven to yield the title compound (11.2 g, 99%) as a white solid: MS (m/z): 177 (M+1).

Preparation 12

Benzyl N-[(3R)-2-oxo-1,3,4,5-tetrahydro-1-benzazepin-3-yl]carbamate

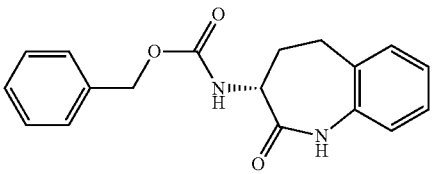

Dissolve potassium carbonate ($K_2CO_3$) (19.50 g, 141.06 mmol)) in water (36 mL) and add it to a solution of 1-amino-1,3,4,5-tetrahydro-2H-benzazepin-2-one HCl salt (6 g, 28.21 mmol) in dichloromethane ($CH_2Cl_2$) (270 mL). Add benzyl chloroformate (6.24 mL, 42.32 mmol) and stir the reaction mixture vigorously at ambient temperature for approximately 16 hours. Collect the precipitate by filtration, wash it with water and ether, and dry it in a vacuum oven to give the title compound (7.2 g, 82%) as a white solid: MS (m/z): 311 (M+1).

Preparation 13

Benzyl N-[(3R)-2-thioxo-1,3,4,5-tetrahydro-1-benzazepin-3-yl]carbamate

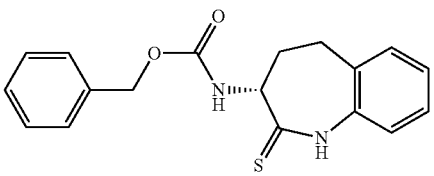

Add Lawesson's Reagent (12.25 g, 30.29 mmol) to a solution of benzyl N-[(3R)-2-oxo-1,3,4,5-tetrahydro-1-benzazepin-3-yl]carbamate (9.4 g, 30.29 mmol) in tetrahydrofuran (470 mL) and stir the reaction under nitrogen for approximately 16 hours at ambient temperature. Remove the precipitate by filtration and discard it. Concentrate the filtrate under reduced pressure and dissolve the residue in ethyl acetate. Wash with water and brine, dry over sodium sulfate, and concentrate the organic layer under reduced pressure to give a thick, yellow oil. Add ether to the thick oil and scratch it to form a solid. Collect the solid by filtration and wash it with ether. Triturate the solid with ether and collect it by filtration to give the title compound (7.28 g, 74%) as a white solid: MS (m/z): 349 (M+23).

Preparation 14

Benzyl N-[(3R)-2-(2,2-dimethoxyethylamino)-4,5-dihydro-3H-1-benzazepin-3-yl]carbamate

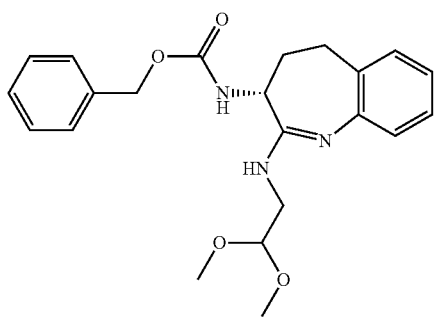

Combine benzyl N-[(3R)-2-thioxo-1,3,4,5-tetrahydro-1-benzazepin-3-yl]carbamate (8.71 g, 26.68 mmol), mercury dichloride (HgCl$_2$) (9.42 g, 34.69 mmol), and aminoacetaldehyde dimethyl acetal (11.65 mL, 106.73 mmol;) in tetrahydrofuran (250 mL) and heat to 55° C. for 20 minutes. Cool the mixture to ambient temperature and filter it through diatomaceous earth. Wash the cake with THF and ethyl acetate and concentrate the filtrate under reduced pressure. Dissolve the resulting oil in dichloromethane, wash with warm water (4×) and brine, dry over sodium sulfate, and concentrate the organic layer under reduced pressure to give the title compound (9.78 g, 92%) as a solid: MS (m/z): 398 (M+1).

Preparation 15

Benzyl N-[(4R)-5,6-dihydro-4H-imidazo[1,2-a][1]benzazepin-4-yl]carbamate

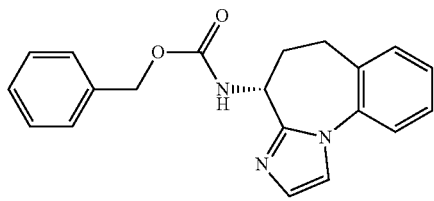

Dissolve benzyl N-[(3R)-2-(2,2-dimethoxyethylamino)-4,5-dihydro-3H-1-benzazepin-3-yl]carbamate (9.78 g, 24.61 mmol) in formic acid (60 mL, 96%) and heat at 100° C. for 1.5 hours. Allow the mixture to cool and remove the black sediment by filtering it through a glass wool plug. Concentrate the filtrate under reduced pressure, pour it into water, and basify it with 1M NaOH. Add ethyl acetate to the resulting precipitate and separate the organic layer. Extract the aqueous layer with ethyl acetate. Combine, wash (brine), dry over sodium sulfate, and concentrate the organic layers under reduced pressure to give the title compound (6.95 g, 85%): MS (m/z): 334 (M+1), 97.8% ee, Retention time for Isomer 1 (R Isomer), 4.58 min; Isomer 2 (S Isomer), 3.20 min. (Chiralpak AD-H column; 100% EtOH with 0.2% dimethylethylamine; flow rate 1.0 mL/min; 225 nM).

Preparation 16

(4R)-5,6-Dihydro-4H-imidazo[1,2-a][1]benzazepin-4-amine

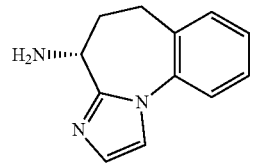

Dissolve benzyl N-[(4R)-5,6-dihydro-4H-imidazo[1,2-a][1]benzazepin-4-yl]carbamate (6.95 g, 20.85 mmol) in absolute ethanol (375 mL, 6.44 moles) and add 10% palladium on carbon (Pd/C) (0.70 g, 6.57 mmol). Place the mixture on a Parr shaker under Hydrogen (H$_2$) for 7 hours (60 psi, ambient temperature). Remove the catalyst by filtration and concentrate the filtrate under reduced pressure to give the title compound (4.17 g, 100%) as a yellow solid: MS (m/z): 200 (M+1).

Scheme C

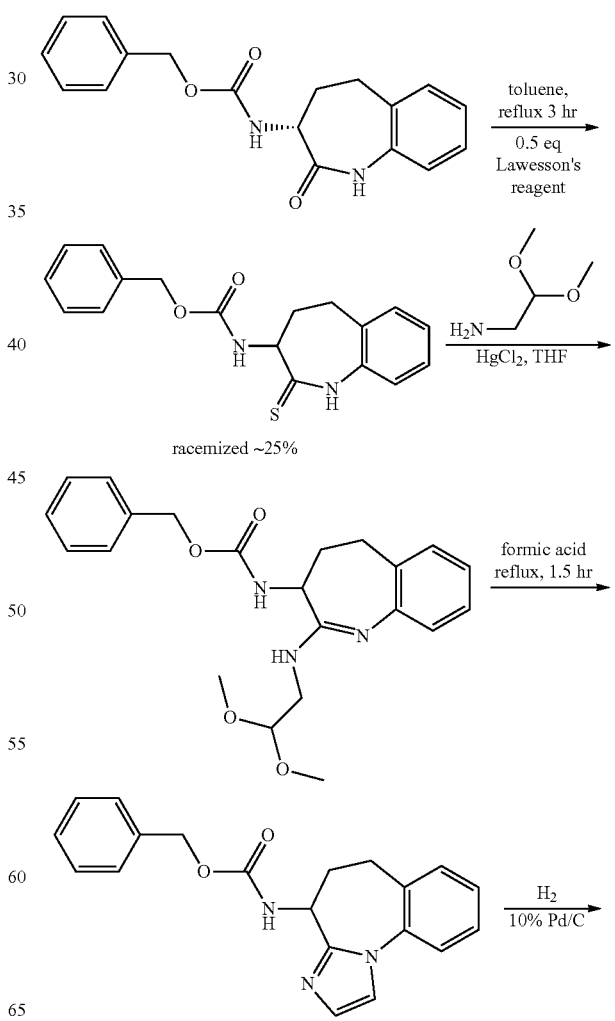

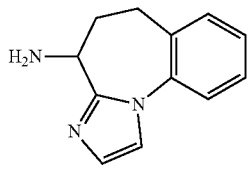

In Scheme C, the synthetic procedure results in a racemic mixture.

Preparation 17

Benzyl N-(2-thioxo-1,3,4,5-tetrahydro-1-benzazepin-3-yl)carbamate

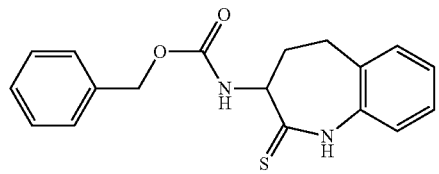

Add Lawesson's Reagent (6.52 g, 16.11 mmol) to a solution of benzyl N-[(3R)-2-oxo-1,3,4,5-tetrahydro-1-benzazepin-3-yl]carbamate (10.0 g, 32.22 mmol) in toluene (120 mL) and heat the reaction under nitrogen at 100° C. for 2.5 hours. Allow the reaction to cool and collect the precipitate by filtration. Wash (ether) the cake and dry it in a vacuum oven to give the title compound (5.5 g, 16.8 mmol). Concentrate the filtrate under reduced pressure and purify it by flash chromatography (30% hexane/$CH_2Cl_2$ to 100% $CH_2Cl_2$) to give the title compound (3.48 g, 10.7 mmol). The compound is partially racemized. The total yield of the title compound is 85%: MS (m/z): 327 (M+1).

Preparation 18

Benzyl N-[2-(2,2-dimethoxyethylamino)-4,5-dihydro-3H-1-benzazepin-3-yl]carbamate

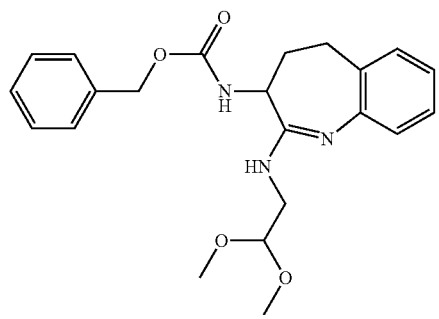

With benzyl N-(2-thioxo-1,3,4,5-tetrahydro-1-benzazepin-3-yl)carbamate (4.2 g, 12.87 mmol) as the starting material, use the method of Preparation 14 to give the title compound (4.68 g, 92%) as a tan solid: MS (m/z): 398 (M+1).

Preparation 19

Benzyl N-(5,6-dihydro-4H-imidazo[1,2-a][1]benzazepin-4-yl)carbamate

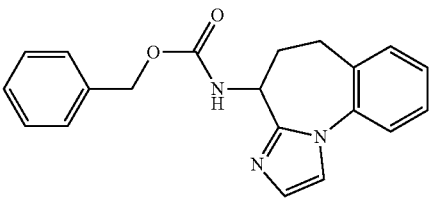

With benzyl N-[2-(2,2-dimethoxyethylamino)-4,5-dihydro-3H-1-benzazepin-3-yl]carbamate (4.6 g, 11.57 mmol) as the starting material, use the method of Preparation 15 to give the title compound (3.8 g, 88%): MS (m/z): 334 (M+1).

Preparation 20

5,6-Dihydro-4H-imidazo[1,2-a][1]benzazepin-4-amine

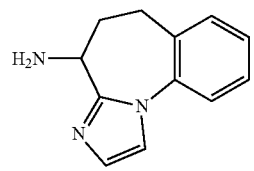

With benzyl N-(5,6-dihydro-4H-imidazo[1,2-a][1]benzazepin-4-yl)carbamate (3.36 g, 10.08 mmol) as the starting material, use the method of Preparation 16 to give the title compound (2.2 g, 100%) as a yellow oil: MS (m/z): 200 (M+1).

Scheme D

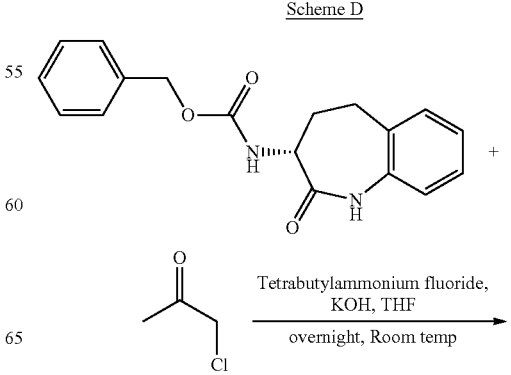

19

-continued

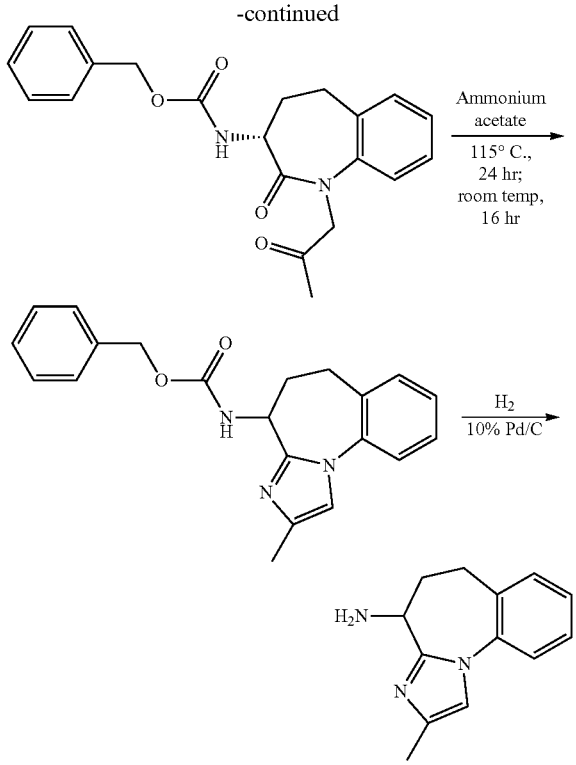

Preparation 21

Benzyl N-[(3R)-1-acetonyl-2-oxo-4,5-dihydro-3H-1-benzazepin-3-yl]carbamate

Add powdered potassium hydroxide (KOH) (0.72 g, 12.89 mmol) to a solution of benzyl N-[(3R)-2-oxo-1,3,4,5-tetrahydro-1-benzazepin-3-yl]carbamate (2.0 g, 6.44 mmol), chloroacetone (1.19 g, 12.89 mmol), and tetrabutylammonium fluoride (1.29 mL, 1.29 mmol, 1M solution in THF) in tetrahydrofuran (65 mL). Stir the mixture for approximately 16 hours at ambient temperature. Add additional potassium hydroxide (0.361 g, 6.44 mmol), chloroacetone (0.59 g, 6.44 mmol), tetrabutylammonium fluoride (0.65 mL, 0.65 mmol, 1M solution in THF) and THF (20 mL) to the reaction and stir for approximately 48 hours at ambient temperature. Filter the reaction mixture through diatomaceous earth and concentrate the filtrate under reduced pressure. Purify the residue by flash chromatography (10% ethyl acetate/hexane to 100% ethyl acetate) to give the title compound (1.64 g, 65%): MS (m/z): 389 (M+23).

20

Preparation 22

Benzyl N-(2-methyl-5,6-dihydro-4H-imidazo[1,2-a][1]benzazepin-4-yl)carbamate

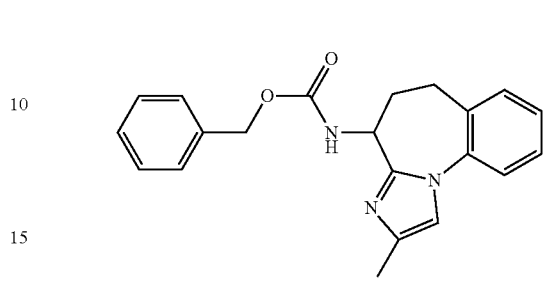

Combine benzyl N-[(3R)-1-acetonyl-2-oxo-4,5-dihydro-3H-1-benzazepin-3-yl]carbamate (0.7 g, 1.91 mmol) with ammonium acetate (2.94 g, 38.2 mmol) in acetic acid (20.0 mL) and heat at 115° C. for 24 hours, and then stir the mixture at ambient temperature for approximately 16 hours. Pour the reaction mixture into ice-water, basify it with ammonium hydroxide (28-30%), and extract with dichloromethane. Wash with water and brine, dry over sodium sulfate, and concentrate the organic layer under reduced pressure. Purify the residue by flash chromatography (10% ethyl acetate/hexane to 50% ethyl acetate/hexane), then an SCX column (methanol, then 10% 2N ammonia in methanol/CH$_2$Cl$_2$) to give the title compound (0.21 g, 32%) as a white solid: MS (m/z): 348 (M+1). (Based on the final compounds made from this intermediate, the title compound is partially racemized.)

Preparation 23

2-Methyl-5,6-dihydro-4H-imidazo[1,2-a][1]benzazepin-4-amine

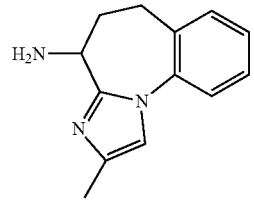

With benzyl N-(2-methyl-5,6-dihydro-4H-imidazo[1,2-a][1]benzazepin-4-yl)carbamate (0.19 g, 0.55 mmol) as the starting material, use the method in Preparation 16 to give the title compound (0.082 g, 69%): MS (m/z): 214 (M+1).

Scheme E

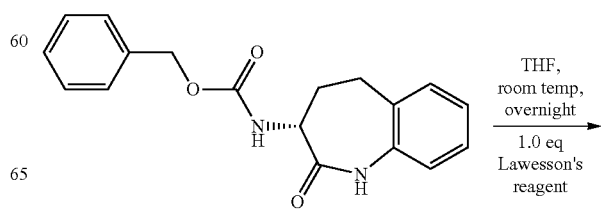

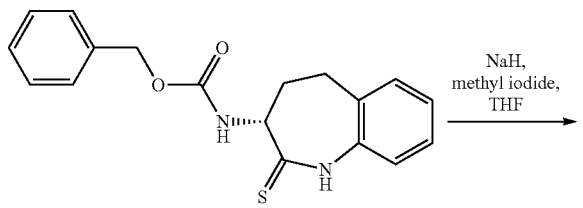

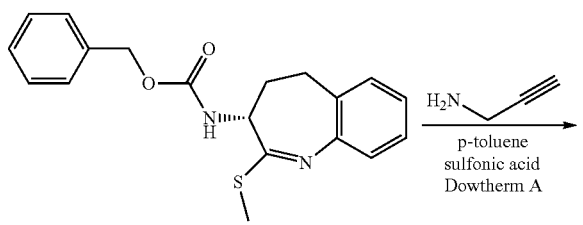

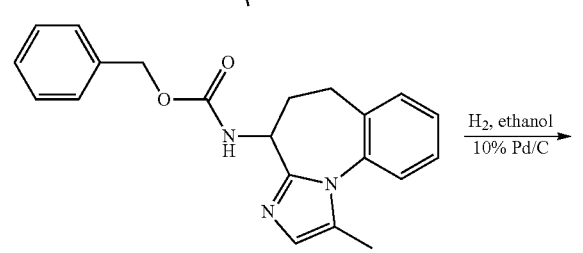

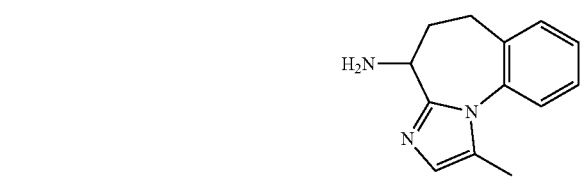

Preparation 24

Benzyl N-[(3R)-2-methylsulfanyl-4,5-dihydro-3H-1-benzazepin-3-yl]carbamate

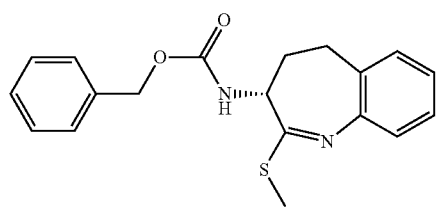

Dissolve benzyl N-[(3R)-2-thioxo-1,3,4,5-tetrahydro-1-benzazepin-3-yl]carbamate (1.5 g, 4.60 mmol) in THF (40 mL), cool to 0° C., and add sodium hydride (NaH) (192.9 mg, 4.83 mmol, 60% in mineral oil) all at once. Remove the bath and stir the reaction for approximately 1 hour under nitrogen. Add methyl iodide (300 μL, 4.83 mmol) and stir for approximately 1 hour at ambient temperature. Concentrate the reaction under reduced pressure to remove most of the THF, dilute the residue with ethyl acetate, and wash with saturated sodium bicarbonate and brine, dry over sodium sulfate, and concentrate the organic layers under reduced pressure to give the title compound (1.5 g, 96%) as a white solid: MS (m/z): 341 (M+1).

Preparation 25

Benzyl N-(1-methyl-5,6-dihydro-4H-imidazo[1,2-a][1]benzazepin-4-yl)carbamate

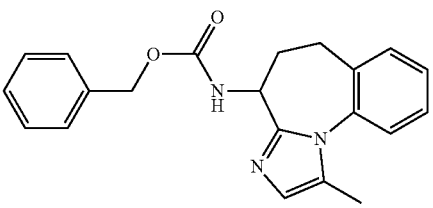

Combine benzyl N-[(3R)-2-methylsulfanyl-4,5-dihydro-3H-1-benzazepin-3-yl]carbamate (500 mg, 1.47 mmol), propargylamine (197.28 μL, 2.94 mmol), and p-toluenesulfonic acid monohydrate (30 mg, 157.71 μmoles) in phenyl ether-biphenyl mixture (2 mL, 6.53 mmol) (Dowtherm A) and stir the mixture for approximately 45 minutes at 180° C. Cool the reaction, and add ether (20 mL), then 2M HCl (20 mL). Stir for a few minutes, remove the aqueous layer, and extract the organic layer with 2N HCl (2×). Combine the aqueous layers and basify with ammonium hydroxide (28%) until alkaline. Collect the precipitate by filtration, wash it with water, and dry it in a vacuum oven. Purify the precipitate by flash chromatography (50% of a 5% solution of ammonia/methanol (2M) in dichloromethane to 90% of the 5% solution) to give the title compound (358 mg, 70%) as an off white solid: MS (m/z): 348 (M+1). Retention time for Isomer 1 (S Isomer)= 3.3 min; Isomer 2 (R Isomer)=3.7 min. (Chiralpak AD-H column; 100% EtOH with 0.2% dimethylethylamine; flow rate 1.0 mL/min; 225 nM). Chiral analysis indicates about 20% racemization.

Preparation 26

1-Methyl-5,6-dihydro-4H-imidazo[1,2-a][1]benzazepin-4-amine

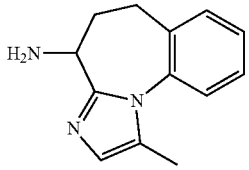

Combine benzyl N-(1-methyl-5,6-dihydro-4H-imidazo[1,2-a][1]benzazepin-4-yl)carbamate (0.99 g, 2.85 mmol) and 10% Pd/C (200 mg, 1.88 mmol) in absolute ethanol (50 mL). Place the mixture on a Parr shaker for 7 hours (hydrogen (H$_2$) 60 psi, ambient temperature). Remove the catalyst by filtration, add 10% Pd/C (200 mg, 1.88 mmol) to the filtrate, and place the mixture on a Parr shaker for 7 additional hours (60 psi, ambient temperature). After 7 hours, add more 10% Pd/C (189 mg, 1.78 mmol) and shake for 7 additional hours. Remove the catalyst by filtration and concentrate the filtrate under reduced pressure to give the title compound (0.53 g, 87%): MS (m/z): 214 (M+1).

Scheme F

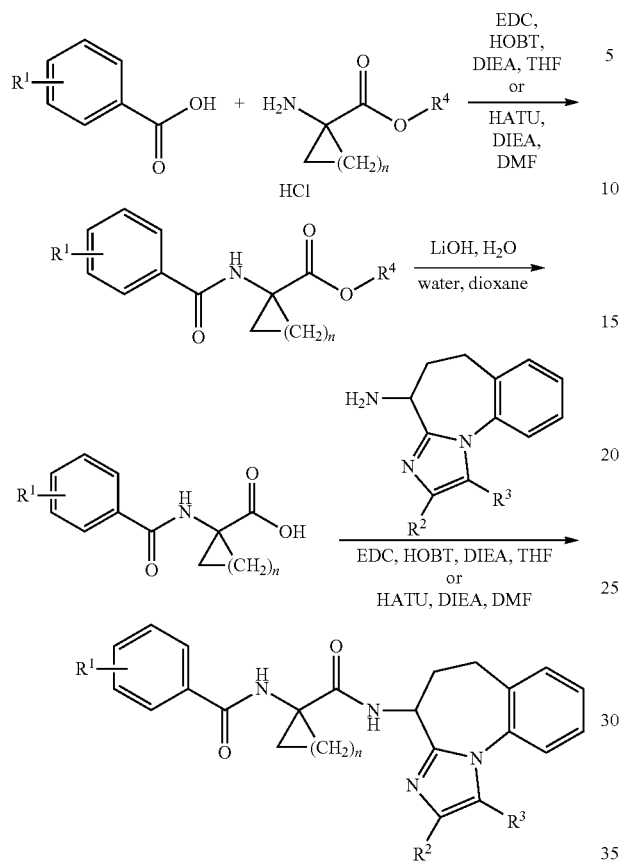

In Scheme F, $R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —$OCF_3$; $R^2$ is selected from the group consisting of H and $CH_3$; $R^3$ is selected from the group consisting of H and $CH_3$, provided that at least one of the group consisting of $R^2$ and $R^3$ is H; n=1, 2, or 3; and $R^4$ may be $CH_3$ or $CH_2CH_3$. Preferably, $R^4$ is $CH_2CH_3$.

Preparation 27

1-Bromo-4-vinyloxy-benzene

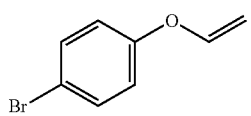

To a mixture of 4-bromophenol (75 g, 433.5 mmol), acetic acid ethenyl ester (80.5 mL, 867.0 mmol) and sodium carbonate (27.6 g, 260.10 mmol) in toluene (430 mL) add di-mu-chlorobis((1,2,5,6-eta)-1,5-cyclooctadiene)diiridium (2.9 g, 4.34 mmol) and the heat the mixture at 100° C. for 2.5 hours. Cool the mixture to ambient temperature, dilute with ethyl acetate (EtOAc) (300 mL) and wash once with water (400 mL). Separate the organic portion and wash once with brine (250 mL). Dry the material over sodium sulfate, filter, and concentrate under reduced pressure. Purify the crude mixture by flash chromatography (0% to 5% EtOAc/Hex) to give the title compound (63.5 g, 74%): GCMS: 198.

Preparation 28

1-Bromo-4-(cyclopropoxy)benzene

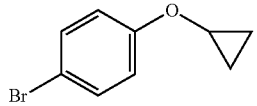

To a 0° C. solution of 1-bromo-4-vinyloxy-benzene (31.75 g, 159.51 mmol) and chloroiodomethane (101.3 g, 574.2 mmol) in 1,2-dichloroethane (410 mL), slowly add diethylzinc (1 M in heptane, 380 mL) over 1 hr while maintaining the temperature below 5° C. Stir the white mixture at 0-5° C. for 2 hours. Quench the reaction slowly at 5° C. with aqueous saturated ammonium chloride (400 mL, exothermic) and separate the layers. Extract the aqueous layer with diethyl ether (2×200 mL). Combine the organic layers, wash with saturated ammonium chloride (400 ml), dry over sodium sulfate, filter, and concentrate under reduced pressure to give the title compound (33 g, 97%) as an oil: GCMS: 212.

Preparation 29

4-(Cyclopropoxy)benzoic acid

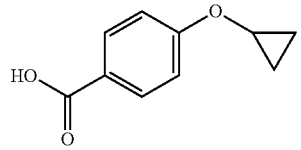

To a −78° C. solution of 1-bromo-4-(cyclopropoxy)benzene (33 g, 154.9 mmol) in tetrahydrofuran (500 mL) add 1.6 M butyl lithium in hexane (96.8 mL, 154.9 mmol) while maintaining a temperature below −70° C. Stir the mixture at −78° C. for 20 minutes after the addition. Add dry ice (464.6 mmol) in 3 portions 5 minutes apart. Stir the mixture at −78° C. for 30 minutes. Remove the cooling bath and quench the mixture with 10% sodium hydrogen sulfate (NaHSO$_4$) (200 mL). Warm the mixture to ambient temperature and extract 3× with EtOAc (300 mL). Combine the organics and wash once with brine, dry over sodium sulfate, filter, and concentrate under reduced pressure. Suspend the residue in diethyl ether and filter. Dry the solid in a vacuum oven to give the title compound (12.9 g, 47%): MS (m/z): 179 (M+1).

Preparation 30

Ethyl 1-[[4-(cyclopropoxy)benzoyl]amino]cyclopropanecarboxylate

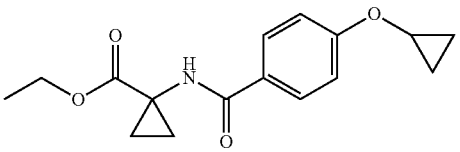

To a 0° C. suspension of 4-cyclopropoxybenzoic acid (24.5 g, 137.3 mmol) in dichloromethane (350 mL) containing 2 drops of DMF, slowly add oxalyl chloride (23.8 mL, 274.7 mmol). After addition, remove the cooling bath and stir for 2 hours. Concentrate the material to dryness under reduced pressure. Dissolve the residue in dichloromethane (500 mL), and then add ethyl 1-aminocyclopropanecarboxylate hydrochloride (Indofine #04-265, 24.9 g, 150.5 mmol) and triethylamine (57.2 mL, 410.4 mmol). Stir the mixture at ambient temperature for approximately 16 hours. Wash the mixture once with 10% NaHSO$_4$ (250 mL). Separate the organic portion and extract the aqueous portion 2× with dichloromethane (200 mL). Combine the organic, dry over sodium sulfate, filter, and concentrate under reduced pressure. Purify the crude mixture by flash chromatography (0% to 45% EtOAc/Hex) to give the title compound (33.7 g, 85%): MS (m/z): 290 (M+1).

Preparation 31

Ethyl 1-[(4-ethoxybenzoyl)amino]cyclopropanecarboxylate

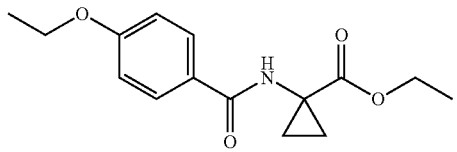

Combine 4-ethoxybenzoic acid (10.0 g, 60.18 mmol), ethyl 1-aminocyclopropanecarboxylate hydrochloride (commercially available, 10.96 g, 66.19 mmol), 1-(3-dimethylaminopropyl)-3-ethylcarbodiimide hydrochloride (EDC) (13.84 g, 72.21 mmol), and 1-hydroxybenzotriazole (HOBT) (9.76 g, 72.21 mmol) in tetrahydrofuran (500 mL). Add diisopropylethylamine (DIEA) (23.09 mL, 132.39 mmol) over 3-5 minutes and stir the reaction for approximately 16 hours at ambient temperature under nitrogen. Dilute the mixture with ethyl acetate, wash with dilute HCl, dilute NaHCO$_3$, and then brine, dry over sodium sulfate, and concentrate the organic layer under reduced pressure. Purify the residue by recrystallization from ethanol to give the title compound (13.93 g, 84%) as a white solid: MS (m/z): 278 (M+1).

The preparations in Table 1 may be prepared essentially as described by the method of Preparation 31 using the reagent in Column 3 in place of 4-ethoxybenzoic acid, and then may be used without purification or undergo purification via recrystallization (ethanol or methanol) or flash chromatography (EtOAc/hexanes gradient ranging from 10-50%). For Preparations 36 and 37, use methyl 1-aminocyclopentanecarboxylate hydrochloride (commercially available) in place of ethyl 1-aminocyclopropanecarboxylate hydrochloride. Preparations 32 and 35 are purified by recrystallization from ethanol. Preparations 33 and 34 are purified by flash chromatography. Preparation 36 may be used without purification. Preparation 37 is purified by recrystallization from methanol.

TABLE 1

| Preparation | Structure and Chemical Name | Reagent | Physical Data MS (m/z): |
|---|---|---|---|
| 32 | ethyl 1-[(4-chlorobenzoyl)amino]cyclopropanecarboxylate | 4-chlorobenzoic acid | 268 (M + 1) |
| 33 | ethyl 1-benzamidocyclopropane carboxylate | benzoic acid | 234 (M + 1) |
| 34 | ethyl 1-[(4-fluorobenzoyl)amino] cyclopropanecarboxylate | 4-fluorobenzoic acid | 248 (M + 1) |
| 35 | ethyl 1-[[4-(difluoromethoxy)benzoyl] amino]cyclopropanecarboxylate | 4-(difluoromethoxy)benzoic acid | 300 (M + 1) |

TABLE 1-continued

| Preparation | Structure and Chemical Name | Reagent | Physical Data MS (m/z): |
|---|---|---|---|
| 36 | 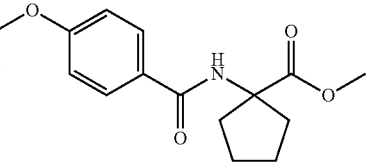<br>Methyl 1-[[4-(difluoromethoxy)benzoyl]amino]cyclopentanecarboxylate | 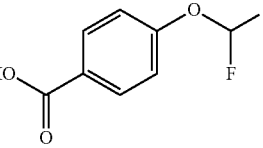 | 314 (M + 1) |
| 37 | 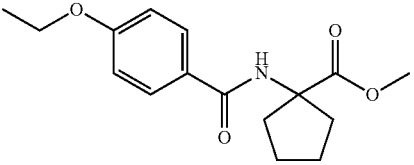<br>Methyl 1-[(4-ethoxybenzoyl)amino]cyclopentanecarboxylate | 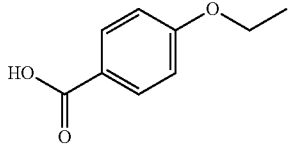 | 292 (M + 1) |

Preparation 38

1-[[4-(cyclopropoxy)benzoyl]amino]cyclopropanecarboxylic acid

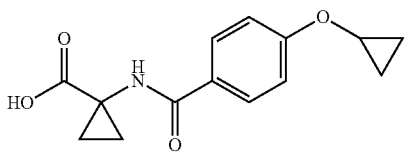

To a solution of ethyl 1-(4-cyclopropoxybenzamido)cyclopropanecarboxylate (33.7 g, 6.48 mmol) in ethanol (380 mL), add sodium hydroxide (174.7 mL, 174.7 mmol) and stir the mixture at 65° C. for 3 hours. Cool the material to ambient temperature and concentrate under reduced pressure to remove the ethanol. Acidify the residue with 10% NaHSO$_4$. Filter the resulting solid and wash with water (3×) and diethyl ether (2×). Dry the material in a vacuum oven to give the title compound (29.9 g, 98%) as a white solid: MS (m/z): 262 (M+1).

Preparation 39

1-[(4-Ethoxybenzoyl)amino]cyclopropanecarboxylic acid

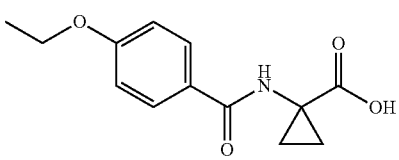

Dissolve ethyl 1-[(4-ethoxybenzoyl)amino]cyclopropanecarboxylate (4.25 g, 15.33 mmol) in 1,4-dioxane (60 mL) and add lithium hydroxide (LiOH) (3.22 g, 76.63 mmol) dissolved in water (30 mL). Stir the reaction for approximately 16 hours at ambient temperature. Concentrate the mixture under reduced pressure, add water, acidify with 5N HCl, and collect the precipitate by filtration to give the title compound (2.8 g, 73%) as a white solid: MS (m/z): 248 (M+1).

The preparations in Table 2 may be prepared essentially as described by the deprotection method of Preparation 39.

TABLE 2

| Preparation | Structure and Chemical Name | Physical Data MS (m/z): |
|---|---|---|
| 40 | 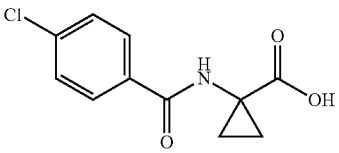<br>1-[(4-chlorobenzoyl)amino]cyclopropanecarboxylic acid | 240 (M + 1) |
| 41 | 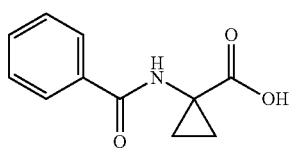<br>1-benzamidocyclopropane carboxylic acid | 240 (M − 1) |
| 42 | 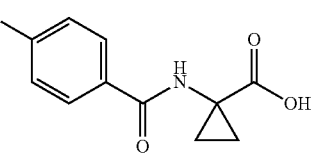<br>1-[(4-fluorobenzoyl)amino]cyclopropanecarboxylic acid | 445 (2M − 1) |

TABLE 2-continued

| Preparation | Structure and Chemical Name | Physical Data MS (m/z): |
|---|---|---|
| 43 | 1-[[4(difluoromethoxy)benzoyl]amino]cyclopropanecarboxylic acid | 272 (M + 1) |
| 44 | 1-[[4-(difluoromethoxy)benzoyl]amino]cyclopentanecarboxylic acid | 298 (M − 1) |
| 45 | 1-[(4-Ethoxybenzoyl)amino]cyclopentanecarboxylic acid | 278 (M + 1) |

EXAMPLE 3

N-[1-[[(4R)-5,6-dihydro-4H-imidazo[1,2-a][1]benzazepin-4-yl]carbamoyl]cyclopropyl]-4-ethoxy-benzamide

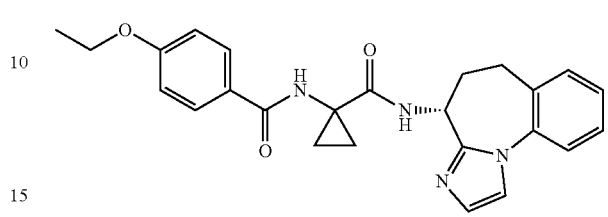

Combine (4R)-5,6-dihydro-4H-imidazo[1,2-a][1]benzazepin-4-amine (0.50 g, 2.51 mmol), 1-[(4-ethoxybenzoyl)amino]cyclopropanecarboxylic acid (0.75 mg, 3.01 mmol), 1-hydroxybenzotriazole (407 mg, 3.01 mmol), and 1-(3-dimethylaminopropyl)-3-ethylcarbodiimide hydrochloride (577 mg, 3.01 mmol) in tetrahydrofuran (40 mL). Add diisopropylethylamine (0.53 mL, 3.01 mmol) and stir the reaction for approximately 16 hours at ambient temperature under nitrogen. Dilute the reaction with ethyl acetate, wash with saturated sodium bicarbonate and brine, dry over sodium sulfate, and concentrate the organic layer under reduced pressure. Purify the residue by flash chromatography (25% EtOAc/hexanes to 100% EtOAc) to give the title compound (860 mg, 80%): MS (m/z): 431 (M+1).

The Examples in Table 3 may be prepared essentially as described by the method of Example 3.

TABLE 3

| Example | Structure and Chemical Name | Physical Data MS (m/z): |
|---|---|---|
| 4 | 4-(difluoromethoxy)-N-[1[[(4R)-5,6-dihydro-4H-imidazo[1,2-a][1]benzazepin-4-yl]carbamoyl]cyclopentyl]benzamide | 481 (M + 1) |
| 5 | 4-chloro-N-[1-(5,6-dihydro-4H-imidazo[1,2-a][1]benzazepin-4-ylcarbamoyl)cyclopropyl]benzamide | 421 (M + 1) |

TABLE 3-continued

| Example | Structure and Chemical Name | Physical Data MS (m/z): |
|---|---|---|
| 6 | 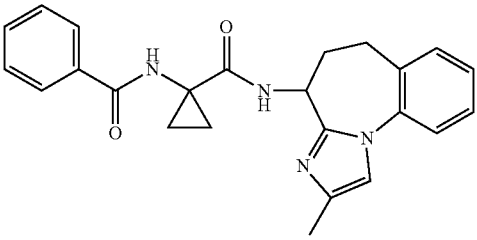<br>N-[1-[(2-methyl-5,6-dihydro-4H-imidazo[1,2-a][1]benzazepin-4-yl)carbamoyl]cyclopropyl]benzamide | 401 (M + 1) |
| 7 | 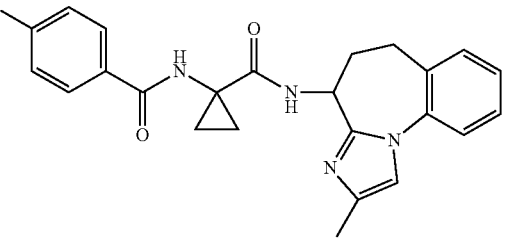<br>4-fluoro-N-[1-[(2-methyl-5,6-dihydro-4H-imidazo[1,2-a][1]benzazepin-4-yl)carbamoyl]cyclopropyl]benzamide | 419 (M + 1) |
| 8 | 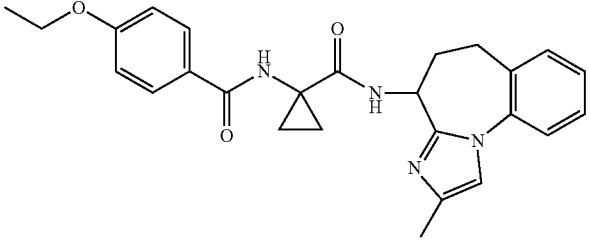<br>4-ethoxy-N-[1-[(2-methyl-5,6-dihydro-4H-imidazo[1,2-a][1]benzazepin-4-yl)carbamoyl]cyclopropyl]benzamide | 445 (M + 1) |
| 9 | 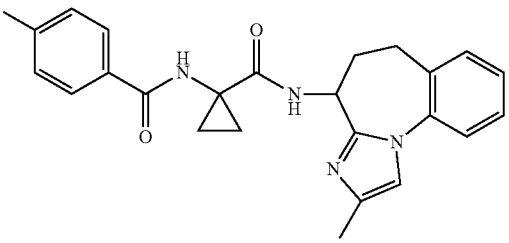<br>4-chloro-N-[1-[(2-methyl-5,6-dihydro-4H-imidazo[1,2-a][1]benzazepin-4-yl)carbamoyl]cyclopropyl]benzamide | 435 (M + 1) |
| 10 | 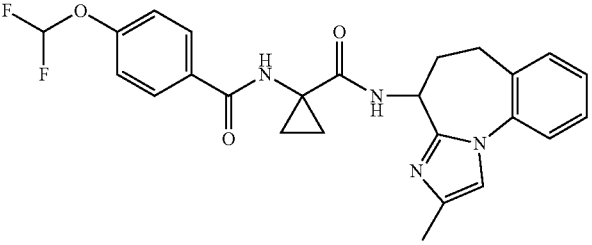<br>4-(difluoromethoxy)-N-[1-[(2-methyl-5,6-dihydro-4H-imidazo[1,2-a][1]benzazepin-4-yl)carbamoyl]cyclopropyl]benzamide | 467 (M + 1) |

TABLE 3-continued

| Example | Structure and Chemical Name | Physical Data MS (m/z): |
|---|---|---|
| 11 | 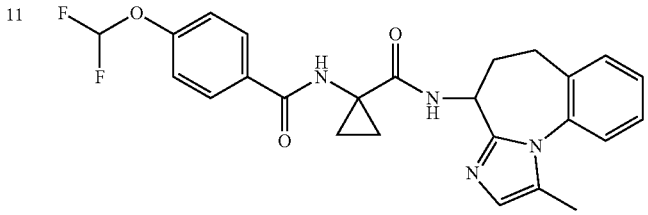<br>4-(difluoromethoxy)-N-[1-[(1-methyl-<br>5,6-dihydro-4H-imidazo[1,2-a][1]benzazepin-4-<br>yl)carbamoyl]cyclopropyl]benzamide | 467<br>(M + 1) |
| 12 | 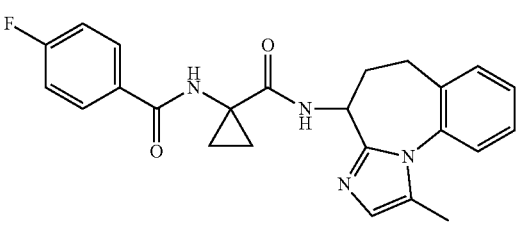<br>4-(fluoro-N-[1-[(1-methyl-5,6-dihydro-<br>4H-imidazo[1,2-a][1]benzazepin-4-<br>yl)carbamoyl]cyclopropyl]benzamide | 419<br>(M + 1) |
| 13 | 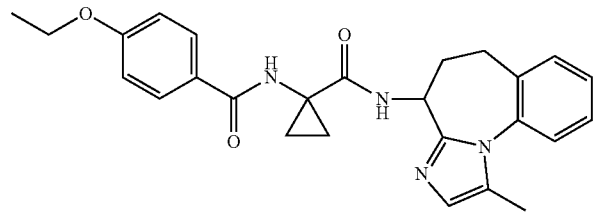<br>4-ethoxy-N-[1-[(1-methyl-5,6-dihydro-<br>4H-imidazo[1,2-a][1]benzazepin-4-<br>yl)carbamoyl]cyclopropyl]benzamide | 445<br>(M + 1) |
| 14 | 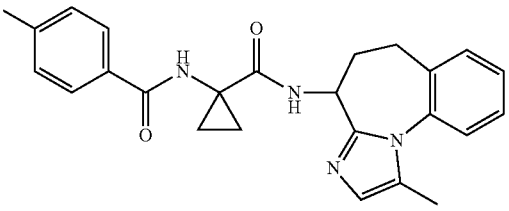<br>4-chloro-N-[1-[(1-methyl-5,6-dihydro-<br>4H-imidazo[1,2-a][1]benzazepin-4-<br>yl)carbamoyl]cyclopropyl]benzamide | 435<br>(M + 1) |
| 15 | 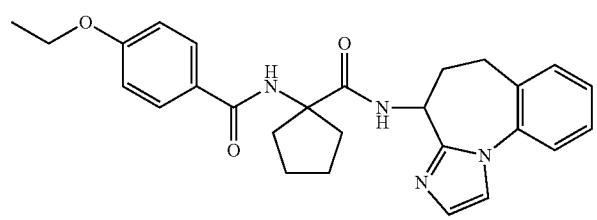<br>N-[1-(5,6-dihydro-4H-imidazo[1,2-a]<br>[1]benzazepin-4-ylcarbamoyl)cyclopentyl]-<br>4-ethoxy-benzamide | 459<br>(M + 1) |

Preparation 46

4-(cyclopropoxy)-N-[1-(5,6-dihydro-4H-imidazo[1,2-a][1]benzazepin-4-ylcarbamoyl)cyclopropyl]benzamide

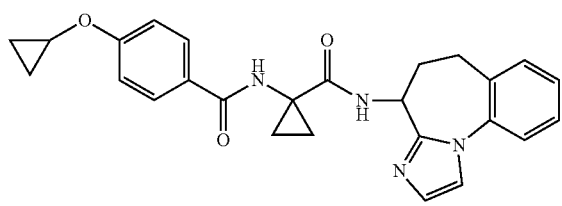

To a mixture of 5,6-dihydro-4H-imidazo[1,2-a][1]benzazepin-4-amine (400 mg, 2.01 mmol), 1-(4-cyclopropoxybenzamido)cyclopropanecarboxylic acid (577 mg, 2.21 mmol), 1-(3-dimethylaminopropyl)-3-ethylcarbodiimide hydrochloride (462 mg, 2.41 mmol) and 1-hydroxybenzotriazole hydrate (369 mg, 2.41 mmol) in dichloromethane (8 mL), add triethylamine (1.26 mL, 9.03 mmol) and stir the mixture at ambient temperature for approximately 16 hours. Purify the crude mixture by flash chromatography (0% to 5% MeOH/dichloromethane) to give the title compound (791 mg, 89%) as a tan foam: MS (m/z): 443 (M+1).

EXAMPLE 16

N-[1-[[(4R)-5,6-dihydro-4H-imidazo[1,2-a][1]benzazepin-4-yl]carbamoyl]cyclopropyl]-4-fluoro-benzamide

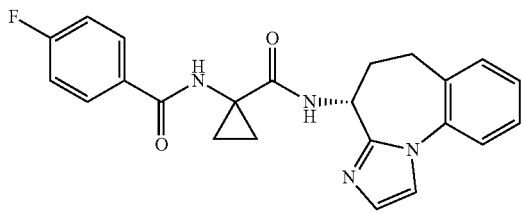

Combine (4R)-5,6-dihydro-4H-imidazo[1,2-a][1]benzazepin-4-amine (95.0 mg, 0.48 mmol), 1-[(4-fluorobenzoyl)amino]cyclopropanecarboxylic acid (128.0 mg, 0.57 mmol), and O—(7-azabenzotriazol-1-yl)-N,N,N',N'-tetramethyluronium hexafluorophosphate (HATU) (218.0 mg, 0.57 mmol) in N,N-dimethylformamide (4 mL). Add diisopropylethylamine (0.21 mL, 1.19 mmol) and stir the reaction for approximately 16 hours at ambient temperature under nitrogen. Dilute the reaction with ethyl acetate, wash with saturated sodium bicarbonate and brine, dry over sodium sulfate, and concentrate the organic layer under reduced pressure. Purify the residue by flash chromatography (3% ammonia (2M) solution in methanol/dichloromethane) to give the title compound (131.0 mg, 68%): MS (m/z): 405 (M+1).

EXAMPLE 17

N-[1-[[(4R)-5,6-dihydro-4H-imidazo[1,2-a][1]benzazepin-4-yl]carbamoyl]cyclopropyl]benzamide

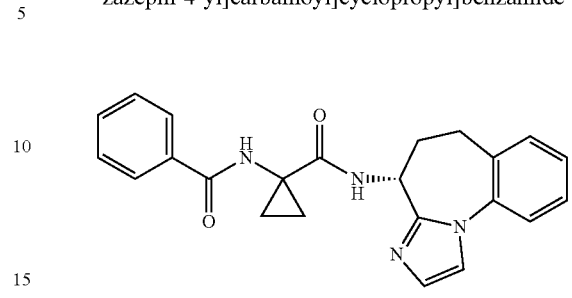

Example 17 may be prepared essentially as described by the method in Example 17. MS (m/z): 387 (M+1). Yield 63%.

Scheme G

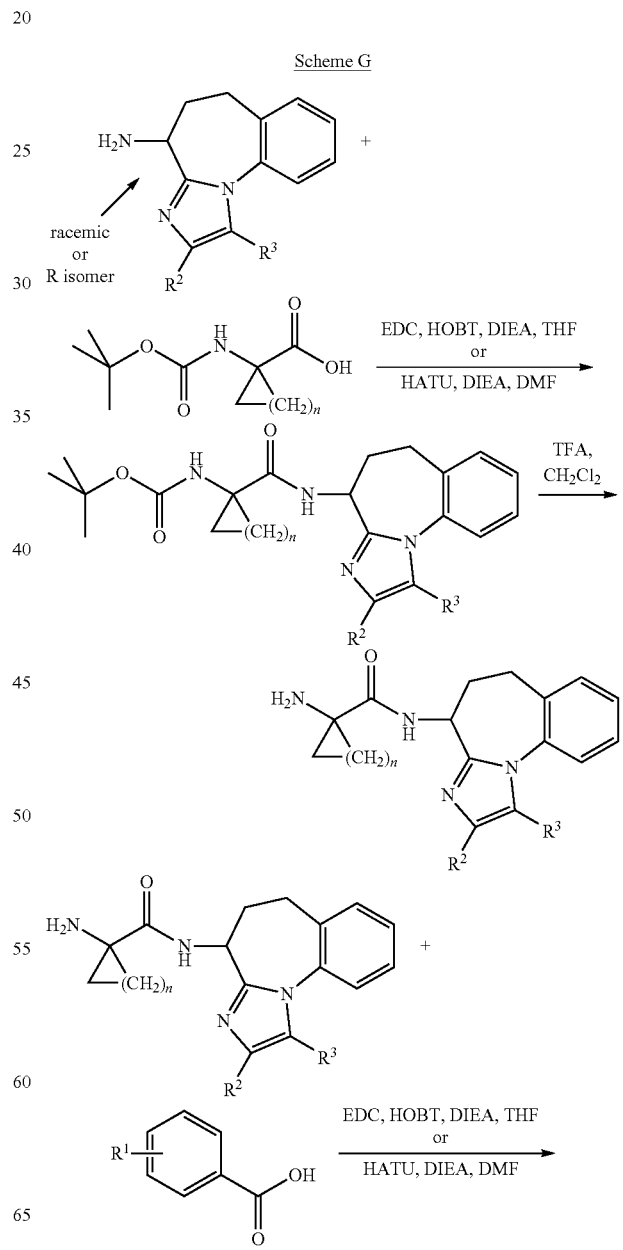

-continued

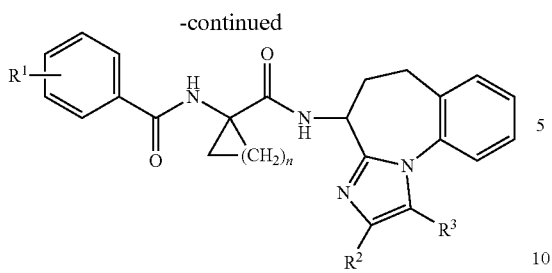

In Scheme G, R¹ is selected from the group consisting of H, F, Cl, —CF$_3$, —CH$_3$, —OH, —O(C$_1$-C$_4$ alkyl), —O-cyclopropyl, —O—CH$_2$-phenyl, —OC(H)F$_2$, and —OCF$_3$; R² is selected from the group consisting of H and CH$_3$; R³ is selected from the group consisting of H and CH$_3$, provided that at least one of the group consisting of R² and R³ is H; and n=1, 2, or 3.

Preparation 47

Tert-butyl N-[1-[[(4R)-5,6-dihydro-4H-imidazo[1,2-a][1]benzazepin-4-yl]carbamoyl]cyclopropyl]carbamate

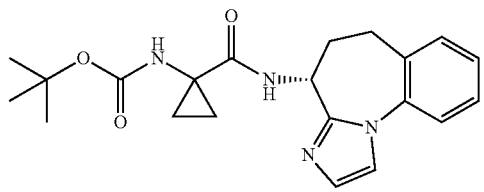

Combine (4R)-5,6-dihydro-4H-imidazo[1,2-a][1]benzazepin-4-amine (570 mg, 2.86 mmol), 1-(tert-butoxycarbonylamino)cyclopropanecarboxylic acid (commercially available, 633.19 mg, 3.15 mmol), 1-hydroxybenzotriazole (464 mg, 3.43 mmol), and 1-(3-dimethylaminopropyl)-3-ethylcarbodiimide hydrochloride (658 mg; 3.43 mmol) in tetrahydrofuran (10 mL). Add diisopropylethylamine (599 µL, 3.43 mmol) and stir the reaction for approximately 16 hours at ambient temperature under nitrogen. Dilute the reaction with ethyl acetate, wash with dilute sodium bicarbonate and brine, dry over sodium sulfate, and concentrate the organic layer under reduced pressure. Purify the residue by flash chromatography (25% EtOAc/hexanes to 85% EtOAc/hexanes) to give the title compound (860 mg, 79%) as a white solid: MS (m/z): 383 (M+1).

Preparation 48

Tert-butyl N-[1-(5,6-dihydro-4H-imidazo[1,2-a][1]benzazepin-4-ylcarbamoyl)cyclopropyl]carbamate

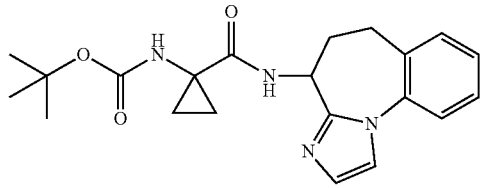

Preparation 48 may be prepared essentially as described by the method of Preparation 47, but using 5,6-dihydro-4H-imidazo[1,2-a][1]benzazepin-4-amine. Purify by flash chromatography using a gradient within the range of 30-95% ethyl acetate/hexane. MS (m/z): 383 (M+1).

Preparation 49

Tert-butyl N-[1-(5,6-dihydro-4H-imidazo[1,2-a][1]benzazepin-4-ylcarbamoyl)cyclopentyl]carbamate

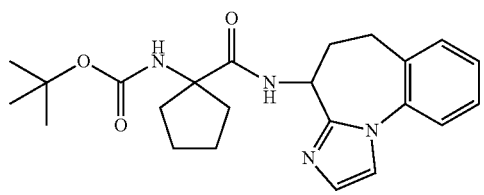

Preparation 49 may be prepared essentially as described by the method of Preparation 47 but using 1-(tert-butoxycarbonylamino)cyclopentanecarboxylic acid (commercially available). Purify by flash chromatography using a gradient within the range of 20-90% ethyl acetate/hexane. MS (m/z): 411 (M+1).

Preparation 50

1-Amino-N-[(4R)-5,6-dihydro-4H-imidazo[1,2-a][1]benzazepin-4-yl]cyclopropanecarboxamide

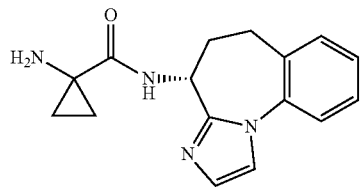

Dissolve tert-butyl N-[1-[[(4R)-5,6-dihydro-4H-imidazo[1,2-a][1]benzazepin-4-yl]carbamoyl]cyclopropyl]carbamate (856 mg, 2.24 mmol) in dichloromethane (20 mL) and cool in an ice bath. Add trifluoroacetic acid (10 mL, 132.25 mmol). Remove the bath and stir the reaction for 1 hr. Concentrate the mixture under reduced pressure and add ethyl acetate. Wash with 1N NaOH and brine, dry over sodium sulfate, and concentrate the organic layer under reduced pressure to give the title compound (470 mg, 74%) as a white solid: MS (m/z): 283 (M+1).

Preparation 51

1-amino-N-(5,6-dihydro-4H-imidazo[1,2-a][1]benzazepin-4-yl)cyclopentanecarboxamide

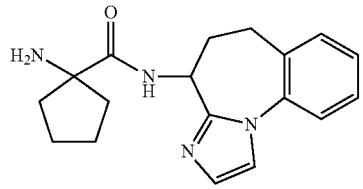

Preparation 51 may be prepared essentially as described by the method of Preparation 50 but using tert-butyl N-[1-(5,6-dihydro-4H-imidazo[1,2-a][1]benzazepin-4-ylcarbamoyl)cyclopentyl]carbamate. MS (m/z): 311 (M−1).

Preparation 52

1-amino-N-(5,6-dihydro-4H-imidazo[1,2-a][1]benzazepin-4-yl)cyclopropanecarboxamide

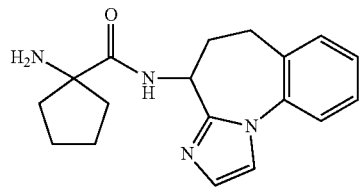

Preparation 52 may be prepared essentially as described by the method of Preparation 50, but using tert-butyl N-[1-(5,6-dihydro-4H-imidazo[1,2-a][1]benzazepin-4-ylcarbamoyl)cyclopropyl]carbamate. MS (m/z): 283 (M+1).

EXAMPLE 18

4-Chloro-N-[1-(5,6-dihydro-4H-imidazo[1,2-a][1]benzazepin-4-ylcarbamoyl)cyclopentyl]benzamide

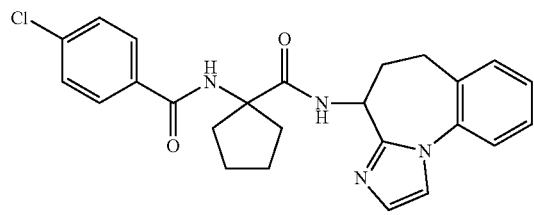

Combine 1-amino-N-(5,6-dihydro-4H-imidazo[1,2-a][1]benzazepin-4-yl)cyclopentanecarboxamide (158 mg, 509.02 μmoles), 4-chlorobenzoic acid (95.64 mg, 610.83 μmoles), 1-(3-dimethylaminopropyl)-3-ethylcarbodiimide hydrochloride (117.10 mg, 610.83 μmoles), and 1-hydroxybenzotriazole (82.54 mg, 610.83 μmoles;) in tetrahydrofuran (12 mL). Add diisopropylethylamine (106.53 μL, 610.83 μmoles) and stir the reaction at ambient temperature for approximately 16 hours. Dilute the reaction with EtOAc, wash with dilute sodium bicarbonate and brine, dry over sodium sulfate, and concentrate the organic layer under reduced pressure. Purify the residue by flash chromatography (0-40% of a 5% solution of ammonia/methanol/dichloromethane (2N)/dichloromethane) to give the title compound (101.0 mg, 44%): MS (m/z): 449 (M+1).

The Examples in Table 4 may be prepared essentially as described by the method of Example 18 but using the reagents listed in column 3. For purification, use flash chromatography using a 5% ammonia (2M) solution in methanol in dichloromethane/dichloromethane gradient ranging from 0-80%.

TABLE 4

| Example | Structure and Chemical Name | Reagents | Physical Data MS (m/z): |
|---|---|---|---|
| 19 | N-[1-(5,6-dihydro-4H-imidazo[1,2-a][1]benzazepin-4-ylcarbamoyl)cyclopentyl]benzamide | 1-amino-N-(5,6-dihydro-4H-imidazo[1,2-a][1]benzazepin-4-yl)cyclopentanecarboxamide and benzoic acid | 415 (M + 1) |
| 20 | 4-(difluoromethoxy)-N-[1-(5,6-dihydro-4H-imidazo[1,2-a][1]benzazepin-4-ylcarbamoyl)cyclopropyl]benzamide | 1-amino-N-(5,6-dihydro-4H-imidazo[1,2-a][1]benzazepin-4-yl)cyclopropanecarboxamide and 4-(difluoromethoxy)benzoic acid | 452 (M + 1) |

EXAMPLE 21

4-Chloro-N-[1-[[(4R)-5,6-dihydro-4H-imidazo[1,2-a][1]benzazepin-4-yl]carbamoyl]cyclopropyl]benzamide

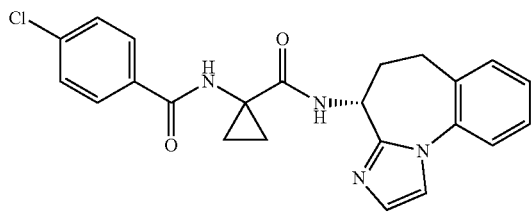

Combine 1-amino-N-[(4R)-5,6-dihydro-4H-imidazo[1,2-a][1]benzazepin-4-yl]cyclopropanecarboxamide (160 mg, 0.57 mmol), 4-chlorobenzoic acid (106 mg, 0.68 mmol) and O-(7-azabenzotriazol-1-yl)-N,N,N',N'-tetramethyluronium hexafluorophosphate (HATU) (259.0 mg, 0.68 mmol;) in N,N-dimethylformamide (4 mL). Add diisopropylethylamine (DIEA) (0.25 mL, 1.42 mmol) and stir the reaction at ambient temperature for approximately 5 hours under nitrogen. Dilute the reaction with ethyl acetate, wash with sodium bicarbonate, water (2×), and brine, dry over sodium sulfate, and concentrate the organic layer under reduced pressure. Purify the residue by flash chromatography (40% EtOAc/hexanes to 100% EtOAc) to give the title compound (190.0 mg, 80%): MS (m/z): 421 (M+1).

The Examples in Table 5 may be prepared essentially as described by the method of Example 21 using the reagent in Column 3 in place of 4-chlorobenzoic acid and using approximately 16 hour reaction times using chiral and racemic amines. Purification is done by flash chromatography using either (Method 1; Examples 22, 23, 24, 25, 27, 28, 29, 30, 31 and 32): a 3-5% ammonia (2M) solution in methanol in dichloromethane/dichloromethane gradient ranging from 0-100% or (Method 2; Examples 26): an ethyl acetate/hexane gradient ranging from 25-90%.

| Example | Structure and Chemical Name | Reagent | Physical Data MS (m/z): |
|---|---|---|---|
| 22 | 2-chloro-N-[1-[[(4R)-5,6-dihydro-4H-imidazo[1,2-a][1]benzazepin-4-yl]carbamoyl]cyclopropyl]benzamide | 2-chloro benzoic acid | 421 (M + 1) |
| 23 | 3-chloro-N-[1-[[(4R)-5,6-dihydro-4H-imidazo[1,2-a][1]benzazepin-4-yl]carbamoyl]cyclopropyl]benzamide | 3-chloro benzoic acid | 421 (M + 1) |
| 24 | N-[1-[[(4R)-5,6-dihydro-4H-imidazo[1,2-a][1]benzazepin-4-yl]carbamoyl]cyclopropyl]-3-ethoxy-benzamide | 3-ethoxy benzoic acid | 431 (M + 1) |

| Example | Structure and Chemical Name | Reagent | Physical Data MS (m/z): |
|---|---|---|---|
| 25 | 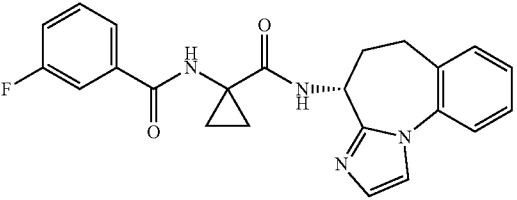<br>N-[1-[[(4R)-5,6-dihydro-4H-imidazo[1,2-a][1]benzazepin-4-yl]carbamoyl]cyclopropyl]-3-fluoro-benzamide | 3-fluoro benzoic acid | 405 (M + 1) |
| 26 | 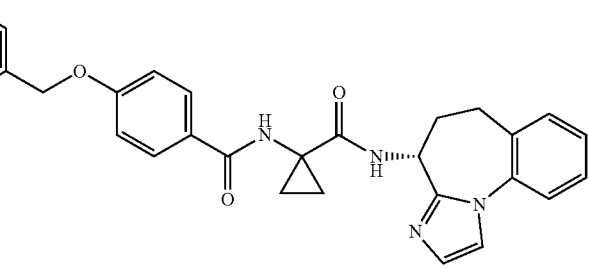<br>4-benzyloxy-N-[1-[[(4R)-5,6-dihydro-4H-imidazo[1,2-a][1]benzazepin-4-yl]carbamoyl]cyclopropyl]benzamide | 4-benzyloxy benzoic acid | 493 (M + 1) |
| 27 | 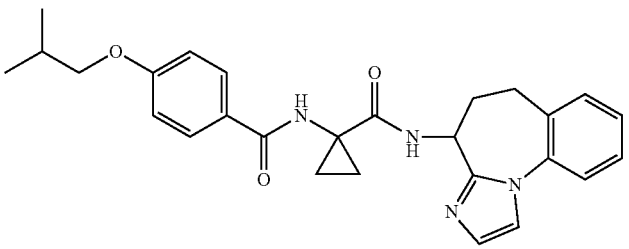<br>N-[1-(5,6-dihydro-4H-imidazo[1,2-a][1]benzazepin-4-ylcarbamoyl)cyclopropyl]-4-isobutoxy-benzamide | 4-isobutoxy benzoic acid | 459 (M + 1) |
| 28 | 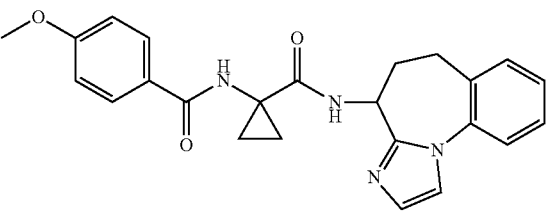<br>N-[1-(5,6-dihydro-4H-imidazo[1,2-a][1]benzazepin-4-ylcarbamoyl)cyclopropyl]-4-methoxy-benzamide | 4-methoxy benzoic acid u | 417 (M + 1) |
| 29 | 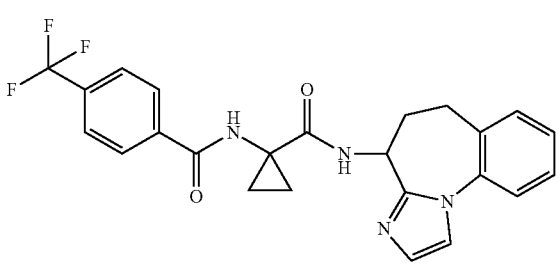<br>N-[1-(5,6-dihydro-4H-imidazo[1,2-a][1]benzazepin-4-ylcarbamoyl)cyclopropyl]-4-(trifluoromethyl)benzamide | 4-trifluoro methyl benzoic acid | 455 (M + 1) |

-continued

| Example | Structure and Chemical Name | Reagent | Physical Data MS (m/z): |
|---|---|---|---|
| 30 | 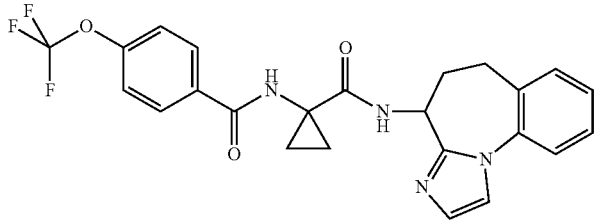<br>N-[1-(5,6-dihydro-4H-imidazo[1,2-a][1]benzazepin-4-ylcarbamoyl)cyclopropyl]-4-(trifluoromethoxy)benzamide | 4-trifluoromethoxy benzoic acid | 471 (M + 1) |
| 31 | 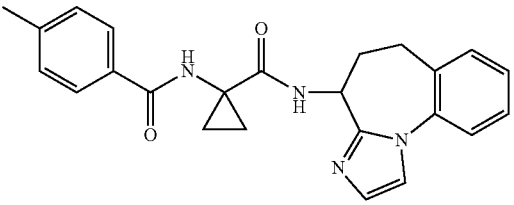<br>N-[1-(5,6-dihydro-4H-imidazo[1,2-a][1]benzazepin-4-ylcarbamoyl)cyclopropyl]-4-methyl-benzamide | 4-methyl benzoic acid | 401 (M + 1) |
| 32 | 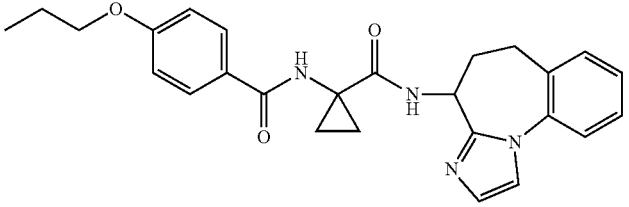<br>N-[1-(5,6-dihydro-4H-imidazo[1,2-a][1]benzazepin-4-ylcarbamoyl)cyclopropyl]-4-propoxy-benzamide | 4-propoxy benzoic acid | 445 (M + 1) |

Scheme H

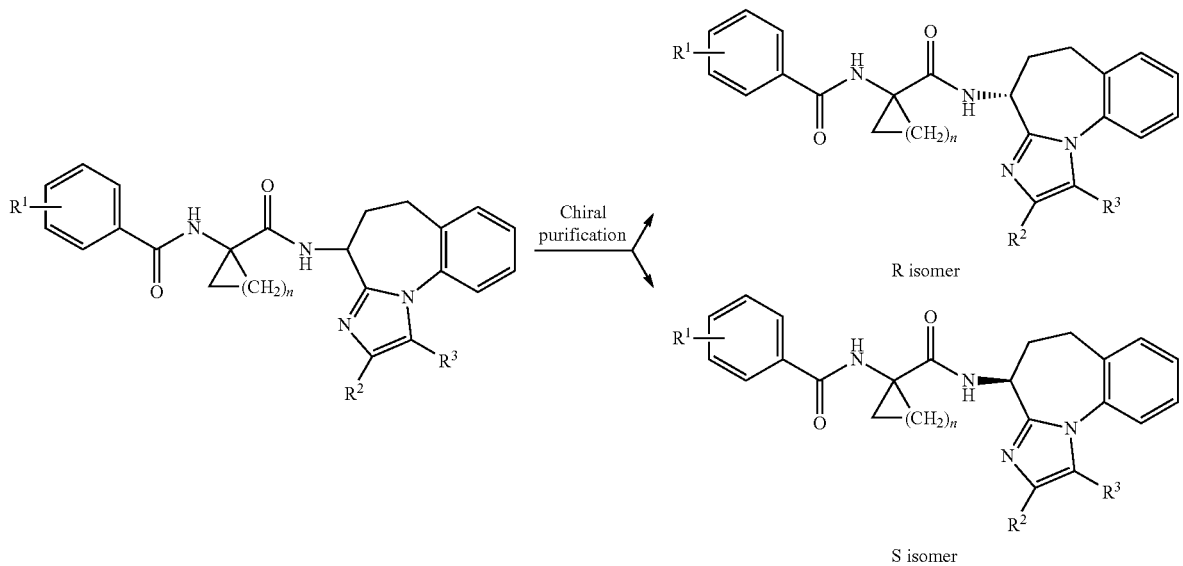

The racemic mixture may be separated and the isomers isolated by the chromatography conditions listed under Methods A, B, C, D, E and F.

Racemic mixtures may be separated into the R and S isomers. Conditions for chiral chromatography:

Method A
SFC—Chiral column: Chiralpak AD-H
Eluent: isocratic conditions with a range of 20-30% ethanol with a 0.2% isopropyl amine modifier and $CO_2$
Signal detected at 225 nM wavelength Method B
SFC—Chiral column: Chiralpak AD-H
Eluent: isocratic conditions with a range of 25-40% isopropanol with a 0.2% isopropyl amine modifier and $CO_2$
Signal detected at 225 nM wavelength Method C
SFC—Chiral column: Chiralpak OD-H
Eluent: isocratic conditions with 20% ethanol with a 0.2% isopropyl amine modifier and $CO_2$
Signal detected at 225 nM wavelength Method D
SFC—Chiral column: Chiralpak OD-H
Eluent: isocratic conditions with a range of 15-20% methanol with a 0.2% isopropyl amine modifier and $CO_2$
Signal detected at 225 nM wavelength Method E
LC—Chiral column: Chiralpak AD-H
Eluent: isocratic conditions with 100% methanol with a 0.2% isopropyl amine modifier.
Signal detected at 225 nM wavelength Method F
SFC—Chiral column: Chiralcel OJ-H
Eluent: isocratic condition with 10% isopropanol with a 0.2% isopropyl amine modifier and $CO_2$
Signal detected at 225 nM wavelength In Table 6, Examples (second column) are separated into Isomers 1 (R Isomer) and 2 (S Isomer) using the chromatographic methods A, B, C, D, E and F. Examples 29, 30, 20, 8 and 6 are separated using Method A; Examples 10, 13, 18, 19 and 15 are separated using Method B; Examples 14, 12 and 11 are separated using Method C; Example 7 is separated using Method D; Example 9 is separated using Method E; Preparation 47 is separated using Method F. Isomers 1 (R Isomer) and 2 (S Isomer), the Example number of the Isomer, and the retention times of the isomers are shown in Column 1

TABLE 6

| Isomers, Example Numbers, and Retention Times (min) | Example number separated | Chemical Name | Physical Data MS (m/z): |
|---|---|---|---|
| Isomer 1 (Example 33) = 1.63; Isomer 2 = 1.15 | 29 | N-[1-[[(4R)-5,6-dihydro-4H-imidazo[1,2-a][1]benzazepin-4-yl]carbamoyl]cyclopropyl]-4-(trifruoromethyl)benzamide | 455 (M + 1) |
| Isomer 1 (Example 34) = 2.03 Isomer 2 = 1.47 | 30 | N-[1-[[(4R)-5,6-dihydro-4H-imidazo[1,2-a][1]benzazepin-4-yl]carbamoyl]cyclopropyl]-4-(trifluoromethoxy)benzamide | 471 (M + 1) |
| Isomer 1 (Example 35) = 3.41 Isomer 2 = 2.32 | 20 | 4-(difluoromethoxy)-N-[1-[[(4R)-5,6-dihydro-4H-imidazo[1,2-a][1]benzazepin-4-yl]carbamoyl]cyclopropyl]benzamide | 471 (M + 1) |
| Isomer 1 (Example 36) = 1.03 Isomer 2 = 1.49 | 10 | 4-(difluoromethoxy)-N-[1-[[(4R)-2-methyl-5,6-dihydro-4H-imidazo[1,2-a][1]benzazepin-4-yl]carbamoyl]cyclopropyl]benzamide | 467 (M + 1) |
| Isomer 1 (Example 37) = 1.17 Isomer 2 = 1.75 | 8 | 4-ethoxy-N-[1-[[(4R)-2-methyl-5,6-dihydro-4H-imidazo[1,2-a][1]benzazepin-4-yl]carbamoyl]cyclopropyl]benzamide | 445 (M + 1) |
| Isomer 1 (Example 38) = 1.05 Isomer 2 = 1.71 | 6 | N-[1-[[(4R)-2-methyl-5,6-dihydro-4H-imidazo[1,2-a][1]benzazepin-4-yl]carbamoyl]cyclopropyl]benzamide | 401 (M + 1) |
| Isomer 1 (Example 39) = 2.40 Isomer 2 = 2.88 | 9 | 4-chloro-N-[1-[[(4R)-2-methyl-5,6-dihydro-4H-imidazo[1,2-a][1]benzazepin-4-yl]carbamoyl]cyclopropyl]benzamide | 435 (M + 1) |
| Isomer 1 (Example 40) = 1.36 Isomer 2 = 2.27 | 7 | 4-fluoro-N-[1-[[(4R)-2-methyl-5,6-dihydro-4H-imidazo[1,2-a][1]benzazepin-4-yl]carbamoyl]cyclopropyl]benzamide | 419 (M + 1) |
| Isomer 1 (Example 41) = 1.34 Isomer 2 = 1.59 | 14 | 4-chloro-N-[1-[[(4R)-1-methyl-5,6-dihydro-4H-imidazo[1,2-a][1]benzazepin-4-yl]carbamoyl]cyclopropyl]benzamide | 435 (M + 1) |
| Isomer 1 (Example 42) = 1.46 Isomer 2 = 1.83 | 13 | 4-ethoxy-N-[1-[[(4R)-1-methyl-5,6-dihydro-4H-imidazo[1,2-a][1]benzazepin-4-yl]carbamoyl]cyclopropyl]benzamide | 445 (M + 1) |
| Isomer 1 (Example 43) = 1.45 Isomer 2 = 1.84 | 12 | 4-fluoro-N-[1-[[(4R)-1-methyl-5,6-dihydro-4H-imidazo[1,2-a][1]benzazepin-4-yl]carbamoyl]cyclopropyl]benzamide | 419 (M + 1) |
| Isomer 1 (Example 44) = 1.61 | 11 | 4-(difluoromethoxy)-N-[1-[[(4R)-1-methyl-5,6-dihydro-4H-imidazo[1,2- | 467 (M + 1) |

TABLE 6-continued

| Isomers, Example Numbers, and Retention Times (min) | Example number separated | Chemical Name | Physical Data MS (m/z): |
|---|---|---|---|
| Isomer 2 = 1.97 | | a][1]benzazepin-4-yl]carbamoyl]cyclopropyl]benzamide | |
| Isomer 1 (Example 45) = 0.83 Isomer 2 = 1.49 | 18 | 4-chloro-N-[1-[[(4R)-5,6-dihydro-4H-imidazo[1,2-a][1]benzazepin-4-yl]carbamoyl]cyclopentyl]benzamide | 449 (M + 1) |
| Isomer 1 (Example 46) = 1.15 Isomer 2 = 1.87 | 19 | N-[1-[[(4R)-5,6-dihydro-4H-imidazo[1,2-a][1]benzazepin-4-yl]carbamoyl]cyclopentyl]benzamide | 415 (M + 1) |
| Isomer 1 (Example 47) = 1.00 Isomer 2 = 1.80 | 15 | N-[1-[[(4R)-5,6-dihydro-4H-imidazo[1,2-a][1]benzazepin-4-yl]carbamoyl]cyclopentyl]-4-ethoxy-benzamide | 459 (M + 1) |
| Isomer 1 (Example 48) = 1.35 Isomer 2 = 1.76 | Prep 46 | 4-(cyclopropoxy)-N-[1-[[(4R)-5,6-dihydro-4H-imidazo[1,2-a][1]benzazepin-4-yl]carbamoyl]cyclopropyl]benzamide | 443 (M + 1) |

Scheme I

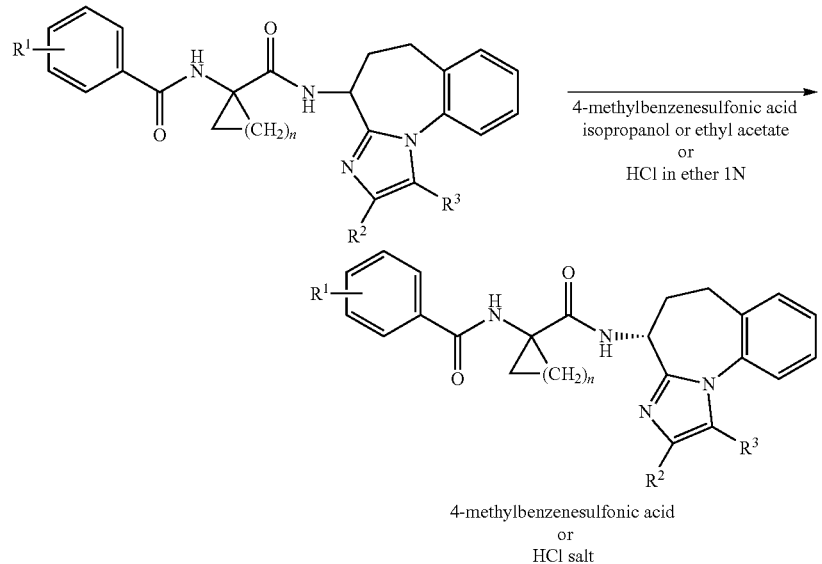

4-methylbenzenesulfonic acid isopropanol or ethyl acetate
or
HCl in ether 1N 4-methylbenzenesulfonic acid
or
HCl salt

EXAMPLE 49

4-Chloro-N-[1-[[(4R)-5,6-dihydro-4H-imidazo[1,2-a][1]benzazepin-4-yl]carbamoyl]cyclopropyl]benzamide; 4-methylbenzenesulfonic acid

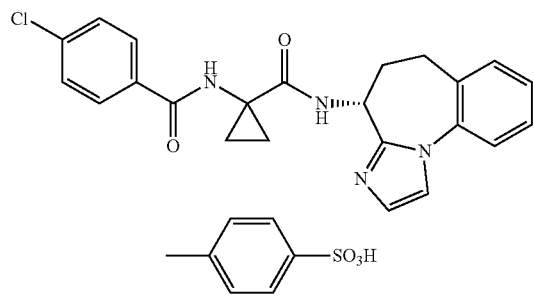

Dissolve 4-chloro-N-[1-[[(4R)-(5,6-dihydro-4H-imidazo[1,2-a][1]benzazepin-4-ylcarbamoyl]cyclopropyl]benzamide (439 mg, 1.04 mmol) in isopropyl alcohol (13.9 mL) and add 4-methylbenzenesulfonic acid monohydrate (198.40 mg, 1.04 mmol) in isopropyl alcohol (1.60 mL) slowly at ambient temperature. Stir the mixture for approximately 2 hours and collect the solid by filtration. Dry it in a vacuum oven to give the title compound (487 mg, 79%) as a white solid: MS (m/z): 421 (M+23).

The Examples in Table 7 may be prepared essentially as described by the Method in Example 49.

TABLE 7

| Example | Example number used to form the salt | Chemical Name | Physical Data MS (m/z): |
|---|---|---|---|
| 50 | 35 | 4-(difluoromethoxy)-N-[1-[[(4R)-5,6-dihydro-4H-imidazo[1,2-a][1]benzazepin-4-yl]carbamoyl]cyclopropyl]benzamide; 4-methylbenzenesulfonic acid | 471 (M + 1) |

TABLE 7-continued

| Example | Example number used to form the salt | Chemical Name | Physical Data MS (m/z): |
|---|---|---|---|
| 51 | 4 | 4-(difluoromethoxy)-N-[1-[[(4R)-5,6-dihydro-4H-imidazo[1,2-a][1]benzazepin-4-yl]carbamoyl]cyclopentyl]benzamide; 4-methylbenzenesulfonic acid | 481 (M + 1) |
| 52 | 34 | N-[1-[[(4R)-5,6-dihydro-4H-imidazo[1,2-a][1]benzazepin-4-yl]carbamoyl]cyclopropyl]-4-(trifluoromethoxy)benzamide; 4-methylbenzenesulfonic acid | 471 (M + 1) |
| 53 | 48 | 4-(cyclopropoxy)-N-[1-[[(4R)-5,6-dihydro-4H-imidazo[1,2-a][1]benzazepin-4-yl]carbamoyl]cyclopropyl]benzamide; 4-methylbenzenesulfonic acid | 443 (M + 1) |

EXAMPLE 54

4-Chloro-N-[1-[[(4R)-5,6-dihydro-4H-imidazo[1,2-a][1]benzazepin-4-yl]carbamoyl]cyclopropyl]benzamide; hydrochloride

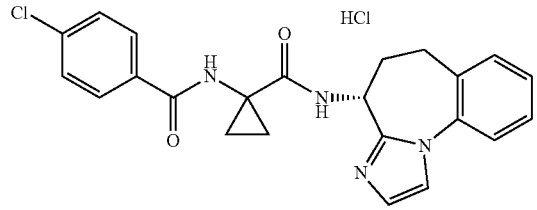

Dissolve 4-chloro-N-[1[[(4R)-(5,6-dihydro-4H-imidazo[1,2-a][1]benzazepin-4-ylcarbamoyl]cyclopropyl]benzamide (350.0 mg, 0.83 mmol) in methyl alcohol (12.0 mL) and cool the solution in an ice bath. Add hydrogen chloride (1N) in ether (3.33 mL, 3.33 mmol) dropwise. Remove the bath, stir the mixture for 30 minutes, and concentrate it under reduced pressure to yield the title compound (323 mg, 85%) as a white solid: MS (m/z): 421 (M+1).

EXAMPLE 55

4-chloro-N-[1-(5,6-dihydro-4H-imidazo[1,2-a][1]benzazepin-4-ylcarbamoyl)cyclopropyl]benzamide hydrochloride

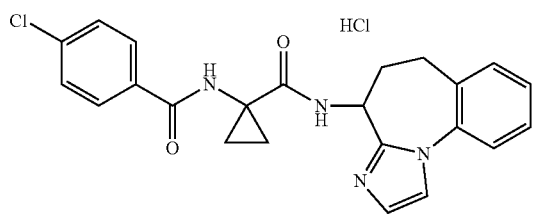

Prepare Example 55 essentially as described in the Method of Example 54. MS (m/z): 421 (M+1).

EXAMPLE 56

N-[1-[[(4R)-5,6-dihydro-4H-imidazo[1,2-a][1]benzazepin-4-yl]carbamoyl]cyclopropyl]-4-hydroxybenzamide

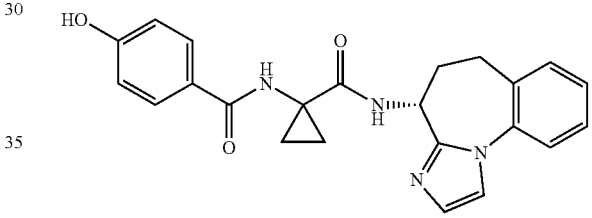

Dissolve 4-benzyloxy-N-[1-[[(4R)-5,6-dihydro-4H-imidazo[1,2-a][1]benzazepin-4-yl]carbamoyl]cyclopropyl]benzamide (145 mg, 294.37 μmoles) in ethanol (20 mL) and hydrogenate on a Parr shaker with 10% Pd/C (22.8 mg, 10.71 μmoles) for 18 hours (60 psi, ambient temperature). Filter off the catalyst and concentrate the filtrate under reduced pressure to give the title compound (107 mg, 90%) as a white solid: MS (m/z): 403 (M+1).

Scheme J depicts an alternate procedure for the synthesis of N-[1-[[(4R)-5,6-dihydro-4H-imidazo[1,2-a][1]benzazepin-4-yl]carbamoyl]cyclopropyl]-4-ethoxy-benzamide.

Scheme J

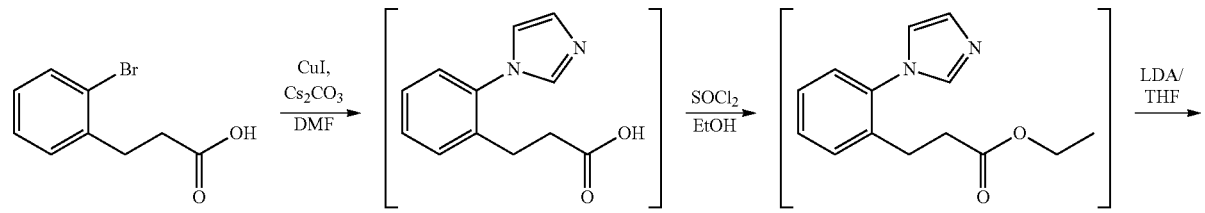

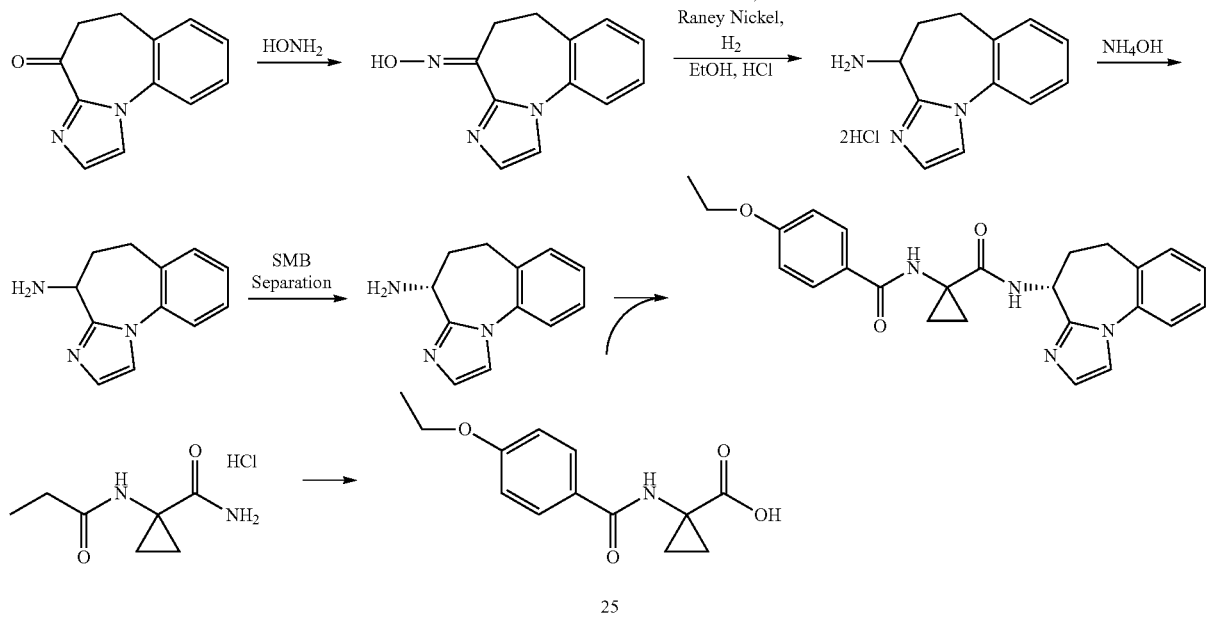

Preparation 53

5,6-dihydroimidazo[1,2-a][1]benzazepin-4-one

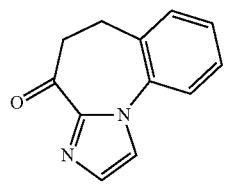

Charge a reactor with 630 kg of DMF, and stir for 1 to 2 hours under a nitrogen bleed. Charge 171 kg of cesium carbonate and 45.0 kg of 3-(2-Bromophenyl)propionic acid, stir the mixture for 1 to 2 hours at 80 to 85° C., and then cool back down to 20 to 25° C. Charge reactor with 27.0 kg of imidazole and 4.4 kg of copper iodide, and stir the mixture for 1 to 2 hours under a nitrogen bleed at 20 to 25° C. Adjust the temperature to 115 to 125° C., and stir vigorously for 20 to 24 hours, [HPLC<3%, 3-(2-Bromophenyl)propionic acid]. Cool the reaction to 60° C., and charge 181 kg of ethanol slowly. Cool reaction to 0 to 15° C. and stir the mixture for 8 to 10 hours. Isolate the solid bi-products by centrifugation. Charge the wet cake, 184 kg of ethanol and 36 kg of DMF into the reactor and stir for 0.5 to 1 hours at 0 to 15° C. Isolate the solid bi-products by centrifugation. Combine the filtrates and transfer to reactor via pipe filter to remove particulates. Concentrate the mixture to 675 to 720 L under reduced pressure, maintaining the internal temp below 65° C. Cool to 25 to 35° C., and charge 174 kg of ethanol into reactor. Stir for 10 to 15 minutes, and check water content of solution (KF value<0.5%).

Charge 95 kg of thionyl chloride slowly into the above solution, maintaining the internal temp between 25 to 40° C. Heat the mixture to reflux for 7 to 10 h [HPLC<3% 3-(2-Imidazol-1-yl-phenyl)-propionic acid]. Cool to 20 to 35° C. Filter the mixture and wash the filter cake with 189 kg of ethanol.

Charge combined filtrates into reactor, and concentrate with agitation under reduced pressure to 675 to 720 L, maintaining the internal temp 65° C. Adjust the temperature to 2030° C. Charge 450 kg of water slowly maintaining the internal temperature at 2030° C., and stir for 10-15 minutes.

Wash the resulting mixture with heptane (3×153 kg), and adjust the pH of the aqueous layer to pH 8.0 using 25% aqueous $Na_2CO_3$ (45 kg), maintaining the internal temperature less than 30° C. Extract the resulting mixture with MTBE (3×450 kg), wash the combined MTBE layers (1×369 kg of 2% $NH_4OH$; 2×362 kg of $H_2O$). Concentrate the organic layer to 90 to 180 L under reduce pressure, maintaining the internal temp below 40° C. Charge 220 kg 2-MeTHF via pipe filter to remove particulates, concentrate to 90 to 180 L under reduce pressure, maintaining the internal temp below 40° C. Charge 214 kg of 2-MeTHF via pipe filter to remove particulates, (in-process KF value<0.2%), and transfer the solution to clean plastic drums to give 195.8 kg solution of ethyl 3-(2-(1H-imidazol-1-yl)phenyl)propanoate in 2-MeTHF.

Charge a reactor with 281 kg of 2-MeTHF and 31 kg of Diisopropylamine Cool to −80 to −70° C., and charge 86 kg of n-butyl lithium in n-hexane slowly maintaining the temperature a at −80 to −70° C. and stir for 1 to 3 h. Charge 195.8 kg solution of ethyl 3-(2-(1H-imidazol-1-yl)phenyl)propanoate in 2-MeTHF into the reactor slowly at −80 to −70° C., and stir for 2 to 4 h at −80 to −70° C. (in process HPLC<3%, ethyl 3-(2-(1H-imidazol-1-yl)phenyl)propanoate). Charge 47.8 kg of ethanol into the reactor slowly at −80 to −70° C., and stir for 0.5 to 2 h at −80 to 70° C. Charge 310 kg of MTBE into the reactor slowly, maintaining internal temp below −25° C. Adjust pH to 7.5 with 292 kg of 10% Citric acid aqueous solution. Adjust the temperature to about 0° C. Separate out aqueous layer, and wash organic layer with 202 kg of 25% NaCl aqueous. Separate the layers, concentrate the organic layer under reduced pressure to 41 to 82 L, maintaining the internal temp below 40° C. Extract the aqueous layer with 200 kg of dichloromethane. Combine the organic layers, and stir for 0.5 to 1 h at 15 to 25° C. Filter through a pad of silicon dioxide (20 kg), and wash the pad with 60 kg of dichloromethane. Concentrate the filtrate under reduced pressure to 82 to 123 L, maintaining the internal temperature below 40°

C. Charge 170 kg of MTBE to the residue, and concentrate under reduced pressure to 82 to 123 L, maintaining the internal temperature below 50° C. Charge 208 kg of MTBE, and stir for 10 to 15 minutes (in-process control indicated 10.8% 2-MeTHF and 4.6% DCM). Charge 279 kg of MTBE and concentrate under reduced pressure to 82 to 123 L, maintaining an internal temperature below 50° C. (residual 2-MeTHF %=1.6%, residual DCM %=2.7%). Charge 14.5 kg of Methyl acetate into the residue, and heat the mixture to reflux for 30 to 60 minutes. Cool the mixture to 0 to 15° C. and stir for 6 to 8 h at 0 to 15° C. Isolate the solid by centrifugation, and wash the cake with 35 kg of MTBE. Dry the resulting solid to give 15.8 kg of 5,6-dihydroimidazo[1,2-a][1]benzazepin-4-one. LC/MS=199 (M+1), 419 (2M+23).

Preparation 54

5,6-dihydro-4H-benzo[f]imidazo[1,2-a]azepin-4-one oxime

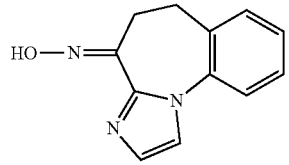

Under a nitrogen atmosphere, charge a reactor with 42 kg of (5,6-dihydroimidazo[1,2-a][1]benzazepin-4-one), 15.5 kg of hydroxylamine hydrochloride, 21.5 kg of sodium acetate anhydrous, and 171 kg of methanol. Heat the resulting brown suspension to 60 to 70° C. for 20 h (in process HPLC<3% 5,6-dihydroimidazo[1,2-a][1]benzazepin-4-one). Cool the reaction to 23 to 25° C. and stir for 8 h. Isolate the solid by centrifugation, rinsing with 33 kg of cold methanol. Transfer the resulting solid into a reactor and slurry with 210 kg of water at 85 to 90° C. for 2 h. Isolate the solid by centrifugation, rinsing the solid with 85 kg of water. Dry the resulting solid to give 39.65 kg of 5,6-dihydro-4H-benzo[f]imidazo[1,2-a]azepin-4-one oxime. MS=214 (M+1).

Preparation 55

5,6-Dihydro-4H-imidazo[1,2-a][1]benzazepin-4-amine dihydrochloride

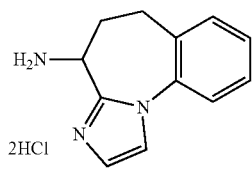

To a reactor with an inert atmosphere, charge 153 kg of methanol, 9.6 kg of 5,6-dihydro-4H-benzo[f]imidazo[1,2-a]azepin-4-one oxime, 1.9 kg of sodium hydroxide solid, 10 kg of water and 10 kg of raney nickel (Suzhou Tailida Sci-tech Co., Ltd.). Pressurize the reactor with hydrogen gas to 58 to 65 psi), and heat to 60 to 65° C. After 40 h, cool to 10-20° C., and filter to remove the nickel catalyst through a pad of 8 kg diatomaceous earth, rinsing with 33 kg of methanol. Concentrate the filtrate under vacuum to between 1 to 2 volumes, holding the reactor temp below 50° C. Charge 130 kg of dichloromethane, and concentrate to 1 to 2 volumes, charge an additional 130 kg of dichloromethane and 104 kg of water. Stir at 10 to 20° C. for 10 to 15 min, and hold without stirring for 30 to 35 min. Separate the layers and transfer the organic and aqueous layers to separate tanks. Wash the organic layer with 104 kg of purified water and 104 kg of 25% sodium chloride solution. Separate the organic layer from the aqueous layer. The original reactor used for the phase separation should be rinsed with a minimal amount of ethanol (20 kg), and the ethanol rinse added to the organic layer. Concentrate the organic layer to 1 to 2 volumes under vacuum, keeping the internal temp below 40° C. Charge 57 to 58 kg of ethanol and concentrate to 1 to 2 volumes, keeping internal temp below 40° C., and repeat until dichloromethane is undetectable by residual solvent analysis (GC). Charge 3 volumes of ethanol, and assay for residual dichloromethane (GC). If there is none detected, cool to 10 to 15° C. and charge 100 kg of 4 N HCl in ethyl acetate slowly. Stir for 3 to 8 hours at 10 to 20° C., filter, and rinse cake with 25 kg of ethanol. Dry the cake at 50 to 55° C. for 12 to 16 h to give 11.1 kg of the racemic amine bis HCl salt (5,6-dihydro-4H-benzo[f]imidazo[1,2-a]azepin-4-amine 1.5-2.0 HCl salt) MS=200 (M+1).

Preparation 56

(4R)-5,6-Dihydro-4H-imidazo[1,2-a][1]benzazepin-4-amine

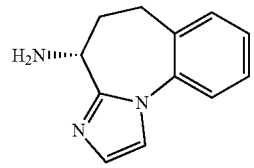

Charge a reactor with 35.9 kg of 5,6-dihydro-4H-imidazo[1,2-a][1]benzazepin-4-amine dihydrochloride and 453 ml of water. Add 29.7 L of NH$_4$OH 25% slowly within 30 minutes maintaining the temperature below 25° C. After the addition, the pH is 9 and is a clear brown solution. Crystallization is induced by adding 31.5 grams of seeds at 22° C. Stir the suspension for 8 hrs and cool to 5° C. Filter and wash the filter cake with 54 L of cold water and dry the resulting filter cake in the filter using N$_2$/vacuum for 31 hrs which yields 5,6-dihydro-4H-imidazo[1,2-a][1]benzazepin-4-amine. Dissolve 29 kg of the crude filter cake in 145 L of ethanol portionwise. Remove 73 L of solvent by vacuum distillation. Add 108 L of ethanol and remove and distillation 133 L of solvent until the final concentration is 2 L/kg. Perform an in-process Karl Fischer analysis to determine the final water content at ≦0.1% w/w.

Perform the SMB separation of 5,6-dihydro-4H-imidazo[1,2-a][1]benzazepin-4-amine on Chiralpak AS-V, 20 Qm, as chiral stationary phase (CSP). The mobile phase is ethanol/methanol/N,N-diethylmethylamine=70:30:0.1 v:v:v. The target enantiomer (4R)-5,6-Dihydro-4H-imidazo[1,2-a][1]benzazepin-4-amine is the second eluting enantiomer. Pool the in-spec fractions of the extract stream and concentrate at To≦65° C. and p=300 to 79 mbar towards a residual volume of ~20%. Pools charged for concentration are passed via charcoal cartridge ZetaCarbon R55SP with downstream inline-filter polycap HD (5.0 µm). [Chiralpak AS-V, 20 µm; Mobile Phase: ethanol/methanol/N,N-diethylmethylamine=70:30:0.1 v:v:v; Feed: ~173 g crude/L in eluent (mobile phase); Extract: 220.60 mL/min; Raffinate: 46.22 mL/min; Eluent: 245.03 mL/min; Feed: 21.80 mL/min;

Recycling: 382.38 mL/min; Period: 1.00 minutes; Temperature: room temperature; Pressure: ~42 bar].

|  | Raffinate | Extract (target enantiomer) |
|---|---|---|
| Chiral purity [% a/a HPLC] | ~92-99 | >99.1 |
| Concentration [g/L] | ~40.8 | ~8.5 |

Preparation 57

Ethyl 1-[(4-ethoxybenzoyl)amino]cyclopropanecarboxylate

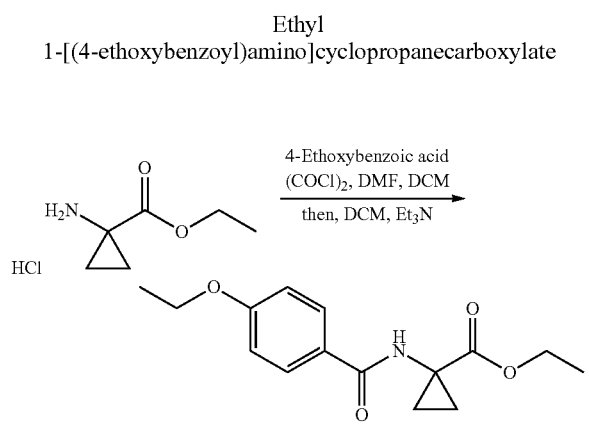

Charge an 800 L reactor with 4-ethoxybenzoic acid (11.0 kg) and dichloromethane (132.6 kg). Add dimethylformamide (34 mL) and then add oxalyl chloride (9.2 kg) over about 45 minutes maintaining the temperature 27±2° C. Stir the contents of reactor at 27±2° C. for 4.5 hours. HPLC analysis shows shows 2.5% of 4-ethoxybenzoic acid. Remove excess oxalyl chloride by vacuum distillation. Dissolve the oily residue in dichloromethane (55 kg). Charge an 800 L reactor with 1-aminocyclopropane-1-carboxylic acid ethyl ester hydrochloride (10 kg) and dichloromethane (110 kg). Charge triethylamine (15.3 kg) and maintain the temperature of less than 10° C. during the addition. Add the acid chloride solution over at least 45 minutes keeping the temperature below 15° C. Stir the resulting mixture at 23° C. overnight (12 hours). HPLC analysis shows about 85% purity. Extract the product slurry with 1N HCl (33.4 L) and extract the aqueous layer with dichloromethane (44.3 kg). Wash the combined organic layers with 8% aqueous $NaHCO_3$ solution (50.4 kg). Wash the organic layer with water (33.4 kg) and brine (33.4 kg). Distill off the dichloromethane until the distillate volume reaches about 70 L, and then add heptanes (164 kg) with good slurry. Continue to distill until the distillate volume reaches additional 70 L of dichloromethane. Batch temperature during this vacuum distillation is as low as 0° C. Stir the product slurry at 20±5° C. for 1 hour. Filter the product, wash with heptanes (2×20 kg), dry under vacuum to yield ethyl 1-[(4-ethoxybenzoyl)amino]cyclopropanecarboxylate (14.6 kg, 86% yield, 93.5% purity by HPLC).

Recrystallization of ethyl 1-[(4-ethoxybenzoyl)amino]cyclopropanecarboxylate:

Charge an 800 L reactor with crude ethyl 1-[(4-ethoxybenzoyl)amino]cyclopropanecarboxylate (14.19 kg) and dichloromethane (144 kg). Stir the mixture 25±2° C. for 30 minutes to give a clear solution. Add Hexanes (191 kg) over a period of 30 minutes into the above solution. Stir the resulting product slurry at 25±2° C. for 20 minutes, then remove dichloromethane by vacuum distillation at 20±5° C. Add additional hexanes (29 kg) for good slurry agitation and stir at 25±2° C. for 1 hour. Filter the solids and wash with hexanes (19 kg, 38 kg, 29 kg and 19 kg). The wet cake of ethyl 1-[(4-ethoxybenzoyl)amino]cyclopropanecarboxylate showed no impurity (4-ethoxybenzoic anhydride) as detected by HPLC analysis. Dry at 40° C. under vacuum for 23 hours to yield ethyl 1-[(4-ethoxybenzoyl)amino]cyclopropanecarboxylate (12.21 kg, 86% recovery yield, 99.9% purity by HPLC) as a white fluffy powder. Proton NMR is consistent with the structure.

Preparation 58

1-[(4-ethoxybenzoyl)amino]cyclopropanecarboxylic acid

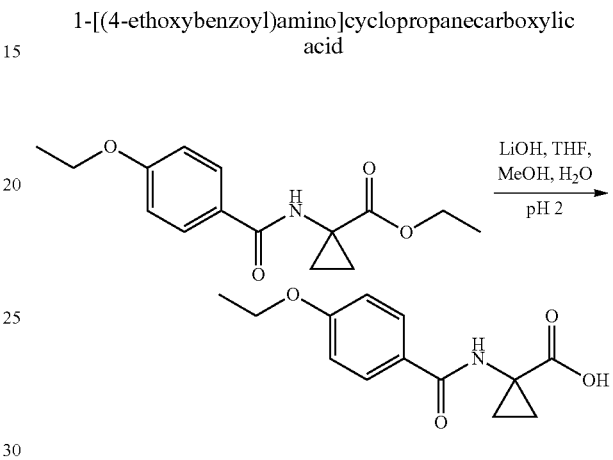

Charge an 800 L reactor with ethyl 1-[(4-ethoxybenzoyl)amino]cyclopropanecarboxylate (12.19 kg), THF (45.5 kg) and MeOH (20.2 kg). Add a solution of LiOH monohydrate (2.49 kg) in water (25.6 kg) to the reactor maintaining the temperature of less than 23° C. during the transfer. Stir the resulting solution at 20±3° C. for overnight (19 h). Remove THF and MeOH by vacuum distillation and then add water (67 kg) to reactor. Adjust the pH of the reaction to pH about 2.0 with 5N HCl (about 12 L) at 17±2° C. Stir the resulting product slurry at 17±2° C. for 50 minutes. Collect the solids by filtration and wash with water (3×40 Kg). Dry the wet cake at 47° C. under vacuum to afford 1-[(4-ethoxybenzoyl)amino]cyclopropanecarboxylic acid (10.74 kg, 98% yield, >99% purity by HPLC, 0.03% KF) as a white powder solid. LC-MS (M+1=250).

EXAMPLE 57

N-[1-[[(4R)-5,6-dihydro-4H-imidazo[1,2-a][1]benzazepin-4-yl]carbamoyl]cyclopropyl]-4-ethoxy-benzamide

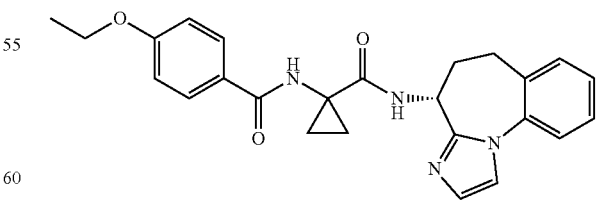

Transfer 46.36 kg ethanolic solution of (4R)-5,6-Dihydro-4H-imidazo[1,2-a][1]benzazepin-4-amine via Zeta-Carbon R55SP charcoal cartridge with downstream inline filter Polycap HD (5.0 μm) in several portions into a 20 L rotavap and concentrate at 55 to 58° C. and p=130 to 079 mbar to finally obtain a solidifying residue. Split the material into two portions (4.524 kg and 4.468 kg).

Dissolve the first portion in 11 kg of dichloromethane and concentrate again at 55° C. and 600 to 200 mbar. After evaporating to dryness, dissolve the resulting solid in 11 kg dichloromethane and the resulting solution is sampled for NMR determination of residual ethanol. Evaporate to dryness at 55° C. and p=600 to 200 mbar. Re-dissolve in 11 kg dichloromethane. Transfer organic solution to a new drum, rinse the rotavap with 5.5 kg dichloromethane and combine the rinse solution with the first concentrate.

Dissolve the second portion in 11 kg of dichloromethane, evaporate at 55° C. and p=600-200 mbar and re-dissolve in 11 kg of dichloromethane. Evaporate to dryness. Re-dissolve in 11 kg dichloromethane and sample for ethanol. Evaporate at 55° C. and p=600 to 200 mbar and then re-dissolve in 11 kg of dichloromethane. Sample for residual ethanol. Combine with the first concentrate. Rinse rotavap with 5.5 kg of dichloromethane; and then combine with the other concentrate solutions. Inertize a 160 L reactor and transfer to the reactor. Charge reactor at 20° C. with 34 L of dichloromethane, 10.4 kg of 1-[(4-ethoxybenzoyl)amino]cyclopropanecarboxylic acid and 17.5 L of triethylamine Cool the resulting solution to −20° C. within 50 minutes. Add 27 L of T3P slowly to the reaction mixture via addition tank within 3 hrs at −20° C. Stir the reaction for 9 hrs at −18° C. Warm the reaction to −3° C. within 40 minutes. Add 42 L of water within 45 minutes, allowing the temperature to rise to 6° C. forming a bright yellow suspension. After 45 minutes at 20° C., the reaction mixture is still a suspension. Add 17 L of dichloromethane to achieve complete dissolution of solids after 20 minutes. After phase separation (25 minutes), remove the aqueous layer (pH 8) and wash the organic dichloromethane phase with 43 L of water. After phase separation, remove the aqueous layer (pH 9). Wash the organic dichloromethane layer a second time with 42 L of water. After phase separation (15 minutes), transfer the organic layer to a new drum. Wash the aqueous layers and transfer into the reactor and wash two times with 21 L of dichloromethane. Combine all organic extract phases in the reactor and use or store at −10° C. for ~5 days. Rinse the reactor with methanol and transfer into the reactor via inline filter. Concentrate the solution to 7.0 L/kg of (4R)-5,6-Dihydro-4H-imidazo[1,2-a][1]benzazepin-4-amine at 65° C. and p=1 bar to 700 mbar, removing 73 L of solvents. Stir the resulting concentrate at 20° C. over night forming a suspension. Dilute the suspension with 66.5 L inline-filtered isopropyl acetate. Concentrate the suspension at 65° C. and p=1 bar and 300 mbar removing 58 L of solvents. Dilute the suspension with 67 L of inline filtered isopropyl acetate at 65° C. and concentrate again at 65° C. and p=300-140 mbar removing 67 L of solvents. Maximum temp during all distillation steps is 50° C. Heat the concentrated suspension to 65° C. within 45 minutes. Add 55 L of inline filtered n-heptane within 35 minutes at 65 to 62° C. Within 12 hrs, stir the suspension at medium velocity cooling down from to 20° C. Filter the suspension via nutsch (fast filtration: 16 minutes). Flush the reactor with 25 L of inline-filtered n-heptane and pass the washing suspension over the filter cake. Blow dry the filter cake and dry under vacuum (p=200-100 mbar) resulting in 16.8 kg N-[1-[[(4R)-5,6-dihydro-4H-imidazo[1,2-a][1]benzazepin-4-yl]carbamoyl]cyclopropyl]-4-ethoxy-benzamide. The NMR of the material of Example 57 is consistent with the material of Example 1.

Preparation 59

5,6-Dihydro-4H-imidazo[1,2-a][1]benzazepin-4-amine

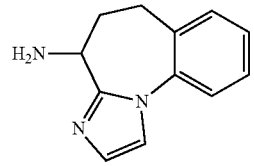

To a 25 mL round bottomed flask under air, add (4S)-5,6-dihydro-4H-imidazo[1,2-a][1]benzazepin-4-amine (1.0 g, 5.02 mmol), sodium t-butoxide (492 mg, 5.12 mmol), PEPPSI™ (37 mg, 0.054 mmol) and a stir bar. Close the flask with a septum and attach it to a double manifold via a needle. Evacuate the flask and backfill with nitrogen three times. Add ethanol (12 mL) via syringe and heat in a 60° C. oil bath for 24 hours. Remove the flask from the oil bath. Add 1 g of silica gel and 400 mg of Si-Thiol metal scavenger and stir for 140 minutes. Filter the mixture through filter paper and concentrate the filtrate via rotary evaporation. Dry the residue at 75° C. under vacuum to yield 1.0 g of tan solid. Chiral LC (10% ethanol/90% heptane with 0.2% DMEA on a Chiralcel OD-H column)-0.2% ee. ES/MS m/z 200.2 [m+H].

EXAMPLE 58

4-Chloro-N-[1-[[(4R)-5,6-dihydro-4H-imidazo[1,2-a][1]benzazepin-4-yl]carbamoyl]cyclopropyl]benzamide

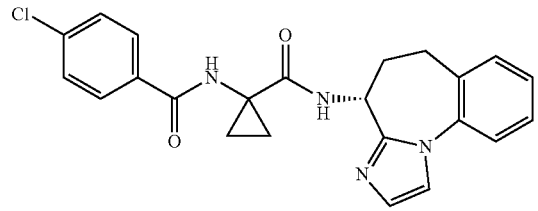

Concentrate the ethanolic solution of (4R)-5,6-Dihydro-4H-imidazo[1,2-a][1]benzazepin-4-amine to dryness prior to use in the coupling reaction. Dissolve 15.0 g (4R)-5,6-Dihydro-4H-imidazo[1,2-a][1]benzazepin-4-amine and 18.03 g 1-[(4-Chlorobenzoyl)amino]cyclopropanecarboxylic acid in 120 ml of dichloromethane and 32 ml triethylamine. After cooling to −20° C., add 53.0 ml (1.2 eq.) of T3P within 40 minutes maintaining a temperature of −19° C. Allow the reaction to warm to room temperature over night. Test by HPLC for complete consumption of starting materials. After aqueous quench (75 ml of water) at 0 to 6° C. and further dilution with dichloromethane (precipitating solids dissolved after adding additional 180 ml of dichloromethane), separate the phases. Wash the organic layer two times with 75 ml of water and then back-extract the combined aqueous layers once with 75 ml of dichloromethane. Concentrate the organic extract phases (420 ml) removing 290 ml of solvents (beginning precipitation of solids). Add 240 ml of isopropyl acetate and then remove a further 250 ml of solvents. Warm the resulting thick suspension to 70° C., add 30 ml of n-heptane and slowly cool the suspension to room temperature over night. Filter the suspension via glass filter nutsch and wash the filter cake with n-heptane. After drying with a rotavap, results in a pale brown solid, 29.65 g (93.58% yield, HPLC (achiral). LC-MS (mass spectrometry) (m/z): 421.

Biological Assays

DGAT-1 enzyme assay Inhibitors of DGAT-1 are identified with an in vitro enzymatic assay which uses recombinant human DGAT-1 expressed in sf9 insect cells as an enzyme source. DGAT-1 enzyme is produced by infecting cells with recombinant baculovirus containing a DGAT-1 expression vector. After 48 hr infection cells are harvested by centrifugation, resuspended in cold 20 mM NaCl, and disrupted with a Dounce homogenizer. Fifteen milliliters of 20 mM NaCl are added to a cell pellet for each liter of infected cell suspension. DNA in the homogenate is sheared by pulling the cell extract through a 25 gauge needle. DGAT-1 activity in the baculovirus infected cell homogenate is compared to homogenate from uninfected cells to assess background enzymatic activity associated with sf9 cells.

Assays are performed in 96 well plates using a modification of the assay described by Coleman (Methods in Enzymology 209. pp 98-102 (1992)). Briefly, compounds are tested in a 1:3 serial dilution scheme from 100 μM to 1.7 nM final concentration. The enzyme reaction mixture contains substrates 250 μM 1,2-sn-diacylglycerol (Avanti Polar Lipids), 5 μM $^{14}C$ oleoyl CoA, and 45 μM oleoyl CoA in an aqueous buffer containing 150 mM Hepes buffer pH7.4, 0.7% vol/vol Triton® X-100 and Complete™ protease inhibitors. Two micrograms of sf9 homogenate is used per reaction well. The total reaction volume is 50 μl. Reactions are incubated at room temperature for 25 minutes and then stopped by the addition of 50 p. 1 of a solution containing 58.8% isopropanol, 14.7% n-heptane, 11.5% water, 12.5% ethanol, and 2.5% 1N sodium hydroxide. One hundred microliters of scintillation cocktail is then added and, after 8 hr, plates are counted. Concentration response curves and $IC_{50}$ values for compounds are derived from the raw data using ActivityBase (IDBS) data analysis software.

All of the compounds of the Examples disclosed herein demonstrate activity in the DGAT-1 enzyme assay substantially as described herein with a measured $IC_{50}$ of less than 600 nM. For the compound N-[1-[[(4R)-5,6-dihydro-4H-imidazo[1,2-a][1]benzazepin-4-yl]carbamoyl]cyclopropyl]-4-ethoxy-benzamide (Examples 1, 3, 57), the measured $IC_{50}$ is 134±8.0 nM (n=2; geometric mean±standard error), and for the compound 4-Chloro-N-[1-[[(4R)-5,6-dihydro-4H-imidazo[1,2-a][1]benzazepin-4-yl]carbamoyl]cyclopropyl]benzamide (Examples 2, 21, 58), the measured $IC_{50}$ is 89.0±0.98 nM (n=3; geometric mean±standard error).

The results from the DGAT-1 enzyme assay demonstrate that the Examples disclosed herein are potent inhibitors of DGAT-1 enzyme.

Adipocyte Triglyceride Synthesis Assay: This assay measures the ability of compounds to inhibit triglyceride synthesis in intact mouse 3T3-L1 adipocytes. Undifferentiated 3T3-L1 cells are cultured in 96 well plates at a density of 25,000 cells per well using standard tissue culture conditions. After two days in culture, the cells are differentiated to adipocytes by placing them in media supplemented with 0.5 mM 1-methyl-3-isobutylxanthine (IBMX), 10 μg/mL insulin and 1 μM dexamethasone. After five days in culture, cells are grown in media supplemented only with 10 μg/mL insulin. Assays are performed after cells have been in culture 12 days. To begin the assay, culture media is removed from the cells and replaced with 50 μl OptiMEM® media containing 0.375 μCi/well $^{14}C$ acetate. Cells are then incubated at 37° C. in 7.5% $CO_2$ for 4 hours. At the end of this incubation, media is removed, cells are washed once with Hank's balanced salts, and 25 μl of 0.7% Triton® X-100 is added to each well and allowed to extract the cells for 5 minutes. At the end of this period, 75 μl of a solution containing 58.8% isopropanol, 14.7% n-heptane, 11.5% water, 12.5% ethanol, and 2.5% 1N sodium hydroxide is added to each well and plates are shaken on an orbital shaker for 2 minutes. 100 μl of heptane is then added and plates are shaken for another 2 minutes. Plates are then spun in a low speed centrifuge to facilitate phase separation and 50 μl of the hydrophobic phase is removed for scintillation counting. Concentration response curves and $EC_{50}$ values for compounds are derived from the raw data using ActivityBase (IDBS) data analysis software. Compounds are tested substantially by the adipocyte triglyceride synthesis assay method described herein.

For the compound N-[1-[[(4R)-5,6-dihydro-4H-imidazo[1,2-a][1]benzazepin-4-yl]carbamoyl]cyclopropyl]-4-ethoxy-benzamide (Examples 1, 3, 57), the measured $EC_{50}$ is 175 nM±94.0 (n=2; geometric mean±standard error). For the compound 4-Chloro-N-[1-[[(4R)-5,6-dihydro-4H-imidazo[1,2-a][1]benzazepin-4-yl]carbamoyl]cyclopropyl]benzamide (Examples 2, 21, 58), $EC_{50}$ is 213 nM±78.2 (n=4; geometric mean±standard error).

The results from the adipocyte triglyceride synthesis assay demonstrate that the compounds N-[1-[[(4R)-5,6-dihydro-4H-imidazo[1,2-a][1]benzazepin-4-yl]carbamoyl]cyclopropyl]-4-ethoxy-benzamide and 4-Chloro-N-[1-[[(4R)-5,6-dihydro-4H-imidazo[1,2-a][1]benzazepin-4-yl]carbamoyl]cyclopropyl]benzamide are potent inhibitors of triglyceride synthesis in intact mouse 3T3-L1 adipocytes.

Oil bolus absorption model: Based on the experiments of Buhman et al. (Journal of Biological Chemistry 277 pp 25474-25479 (2002)) which demonstrated that DGAT-1 is involved in lipid absorption from the small intestine, an in vivo model of DGAT-1 inhibition was developed which measures plasma triglyceride levels following oral administration of an olive oil bolus to rats. Male Sprague-Dawley rats (280-320 g, n=6 per test group) on regular chow are acclimated to the test vivarium for at least 1 week prior to compound evaluation. Prior to compound testing, rats are fasted for 16 hour. Compounds are administered via oral gavage in a vehicle of 10% ethanol/90% corn oil at a volume of 1 ml/kg. Four hours after compound administration, a 0.5 ml blood sample is collected via the tail vein. Immediately following the 4 hour blood collection, a 3.0 ml bolus of olive oil is administered by oral gavage. A final blood sample is collected from the tail vein 6 hours after compound administration. Plasma is prepared from blood samples by centrifugation and analyzed for both triglyceride content, using a Hitachi 912 clinical chemistry analyzer, and test compound levels. The effective dose that reduces the increase in plasma triglyceride by 50% ($ED_{50}$) and 80% ($ED_{80}$) is determined DGAT-1 inhibition is indicative of the ability of the test compound to inhibit the increase in plasma triglyceride that occurs between hours 4 and 6 of the study (between 14 and 16 hours in the modified model) in vehicle treated (control) animals. In a modification of the model, compound is administered 14 hours prior to the first blood sample collection and oil bolus administration. The final blood sample is collected at 16 hours after dosing. In this longer duration version of the model, the 10% ethanol/90% corn oil vehicle is administered, without compound, at 10 hours after compound dosing to be consistent with the shorter duration version of the model. Compounds are tested substantially by the oil bolus absorption rat model method described herein.

For the compound N-[1-[[(4R)-5,6-dihydro-4H-imidazo[1,2-a][1]benzazepin-4-yl]carbamoyl]cyclopropyl]-4-ethoxy-benzamide (Examples 1, 3, 57), the three experiments used doses of 1, 3, 10 and 30 mg/kg. For the compound 4-Chloro-N-[1-[[(4R)-5,6-dihydro-4H-imidazo[1,2-a][1]benzazepin-4-yl]carbamoyl]cyclopropyl]benzamide (Examples 2, 21, 58), experiment 1 used doses of 0.3, 1, 3, 10 and 30 mg/kg, and for experiments 2 and 3, the doses used are 0.1, 0.3, 1, 3 and 10 mg/kg. The results are provided in Tables 8 and 9.

TABLE 8

Results of N-[1-[[(4R)-5,6-dihydro-4H-imidazo[1,2-a][1]benzazepin-4-yl]carbamoyl]cyclopropyl]-4-ethoxy-benzamide (Examples 1, 3, 57) in the 16 hour oil bolus study.

| Experiment | $ED_{50}$ (mg/kg) | Standard error of $ED_{50}$ | $ED_{80}$ (mg/kg) | Standard error of $ED_{80}$ |
|---|---|---|---|---|
| 1 | 12.37 | 2.46 | 19.61 | 7.67 |
| 2 | 2.92 | 0.76 | 7.64 | 3.80 |
| 3 | 1.71 | 0.55 | 5.52 | 2.81 |

TABLE 9

Results of 4-Chloro-N-[1-[[(4R)-5,6-dihydro-4H-imidazo[1,2-a][1]benzazepin-4-yl]carbamoyl]cyclopropyl]benzamide (Examples 2, 21, 58) in the 6 hour oil bolus study.

| Experiment | $ED_{50}$ (mg/kg) | Standard error of $ED_{50}$ | $ED_{80}$ (mg/kg) | Standard error of $ED_{80}$ |
|---|---|---|---|---|
| 1 | 0.73 | 0.24 | 2.22 | 1.15 |
| 2 | 0.57 | 4.52 | ND* | ND* |
| 3 | 0.26 | 0.093 | 0.45 | 0.27 |

ND: Not determined

The data are analyzed using meta-analysis. The overall $ED_{50}$ ($ED_{80}$) is estimated as the weighted average of $ED_{50}$ ($ED_{80}$) from individual studies, with the weights being the inverse of variance of $ED_{50}$ ($ED_{80}$) estimates. The homogeneity Q-test is performed. If the test is significant at 0.10 level, a mixed-effect model is used to include both inter-study and intra-study variability. The weights are adjusted to the inverse of the sum of inter-study variance and the intra-study variance of $ED_{50}$ ($ED_{80}$) from individual studies. The inter-study variance is estimated by the Paule-Mandel estimator. (References: Sutton, A. J., Jones, D. R., Abrams, K. R., Sheldon, T. A., and Song, F., Methods for Meta-analysis in Medical Research London, John Wiley, ISBN 0-471-49066-0 (2000). Dersimonian R., and Kacker, R., Random-effects model for meta-analysis of clinical trials: An update, Contemporary Clinical Trials 28 p 105-114 (2007).

TABLE 10

Meta-Analysis of N-[1-[[(4R)-5,6-dihydro-4H-imidazo[1,2-a][1]benzazepin-4-yl]carbamoyl]cyclopropyl]-4-ethoxy-benzamide (Examples 1, 3, 57) in the 16 hour oil bolus study.

| | Mean (mg/kg) | Standard error | Q-test (p-value) |
|---|---|---|---|
| $ED_{50}$ | 5.30 | 3.27 | 18.48 (p < 0.001) |
| $ED_{80}$ | 7.34 | 2.17 | 2.98 (p = 0.23) |

TABLE 11

Meta-Analysis of 4-Chloro-N-[1-[[(4R)-5,6-dihydro-4H-imidazo[1,2-a][1]benzazepin-4-yl]carbamoyl]cyclopropyl]benzamide (Examples 2, 21, 58) in the 6 hour oil bolus study.

| | Mean (mg/kg) | Standard error | Q-test (p-value) |
|---|---|---|---|
| $ED_{50}$ | 0.32 | 0.09 | 3.35 (p = 0.19) |
| $ED_{80}$ | 0.54 | 0.27 | 2.11 (p = 0.15) |

The results demonstrate that N-[1-[[(4R)-5,6-dihydro-4H-imidazo[1,2-a][1]benzazepin-4-yl]carbamoyl]cyclopropyl]-4-ethoxy-benzamide (Examples 1, 3, 57) and 4-Chloro-N-[1-[[(4R)-5,6-dihydro-4H-imidazo[1,2-a][1]benzazepin-4-yl]carbamoyl]cyclopropyl]benzamide (Examples 2, 21, 58) inhibit the increase in plasma triglyceride in the oil bolus absorption rat model. These results are indicative of inhibition of DGAT-1.

Diet-induced obese mouse model: To measure effects on body weight and food intake, compounds are tested in C57 B16 mice fed a high fat diet (Research Diets D12492). Fourteen week old mice raised on D12492 are acclimated to the test vivarium for 2 weeks on a 12 hour light/dark cycle. Seven days prior to compound testing, animals are dosed by oral gavage either once or twice daily with a suitable vehicle in order to accustom the mice to handling. On day 6 of vehicle dosing, body composition is measured by quantitative nuclear magnetic resonance (QNMR). On day seven of vehicle dosing, animals are randomized by body weight and sorted into test groups (n=8). Compound dosing, twice daily, commences after 7 days of vehicle dosing. Animals are given compound 30 minutes prior to the dark phase of the dark/light cycle and, if desired, again 5.5 hours into the dark phase. Compound dosing continues for 15 to 22 days during which time food intake and body weight are measured daily. On day 14 of the experiment, body composition is measured for a second time by QNMR. On day 15, terminal bleeds are taken from two animals per test group at 0, 2, 4, and 6 hours after the final dose for measurement of test compound levels in plasma.

The data are analyzed using a meta-analysis. For the percent Body Weight gain (loss) and percent Fat Mass gain (loss), the measure of treatment effect in the meta-analysis is the group mean difference between treatment and control group. For the percent Cumulative Food Intake Change from Control (% CFICFC), the measure of treatment effect is % CFICFC itself. The overall treatment effect is estimated as the weighted average of treatment effect from individual studies, with the weights being the inverse of variance of individual study's treatment effect estimates. The homogeneity Q-test is performed. If the test is significant at 0.10 level, then a mixed-effect model is used to include both inter-study and intra-study variability. The weights are adjusted to the inverse of the sum of inter-study variance and the intra-study variance of treatment effect estimates from individual studies. The inter-study variance is estimated by the Paule-Mandel estimator. (References: Sutton, A. J., Jones, D. R., Abrams, K. R., Sheldon, T. A., and Song, F., Methods for Meta-analysis in Medical Research London, John Wiley, ISBN 0-471-49066-0 (2000). Dersimonian R., and Kacker, R., Random-effects model for meta-analysis of clinical trials: An update, Contemporary Clinical Trials 28 p 105-114 (2007). Compounds are tested substantially by the diet-induced obese mouse model method described herein.

For N-[1-[[(4R)-5,6-dihydro-4H-imidazo[1,2-a][1]benzazepin-4-yl]carbamoyl]-4-ethoxy-benzamide (Examples 1, 3, 57), three experiments were performed at doses of 1, 3, 10 and 30 mg/kg (two of the experiments) and 3 and 30 mg/kg (one of the experiments). Because the 3 and 30 mg/kg doses are common to the experiments, these doses are used to compare the results.

For 4-Chloro-N-[1-[[(4R)-5,6-dihydro-4H-imidazo[1,2-a][1]benzazepin-4-yl]carbamoyl]cyclopropyl]benzamide (Examples 2, 21, 58), two experiments were performed at doses of 3, 10, 30 and 60 mg/kg and at 0.3, 1, 3 and 10 mg/kg. For each of the experiments, the doses are given twice per day. Because the 3 and 10 mg/kg doses are common to the experiments, these doses are used to compare the results.

Tables 12, 13 and 14 display the results of the mean percent gain (positive) or loss (minus) in body weight, fat mass, and food intake for N-[1-[[(4R)-5,6-dihydro-4H-imidazo[1,2-a][1]benzazepin-4-yl]carbamoyl]cyclopropyl]-4-ethoxy-benzamide (Examples 1, 3, 57).

TABLE 12

Vehicle controlled percent Body Weight Change

| Dose minus control | Mean (percent) | Standard Error | Q-test (p-value) |
|---|---|---|---|
| 3 mg/kg – control | −4.74 | 0.92 | 0.61 (p = 0.74) |
| 30 mg/kg – control | −5.31 | 0.77 | 0.05 (p = 0.98) |

TABLE 13

Vehicle controlled percent Fat Mass Change

| Dose minus control | Mean (percent) | Standard Error | Q-test (p-value) |
|---|---|---|---|
| 3 mg/kg – control | −6.69 | 1.14 | 1.94 (p = 0.38) |
| 30 mg/kg – control | −8.24 | 1.01 | 0.31 (p = 0.85) |

TABLE 14

Vehicle controlled percent Food Intake Change

| Dose minus control | Mean (percent) | Standard Error | Q-test (p-value) |
|---|---|---|---|
| 3 mg/kg – control | −10.11 | 2.25 | 5.82 (p = 0.05) |
| 30 mg/kg – control | −11.35 | 1.50 | 3.53 (p = 0.17) |

Tables 15, 16 and 17 display the results of the mean percent gain (positive) or loss (minus) in body weight, fat mass, and food intake for 4-Chloro-N-[1-[[(4R)-5,6-dihydro-4H-imidazo[1,2-a][1]benzazepin-4-yl]carbamoyl]cyclopropyl]benzamide (Examples 2, 21, 58).

TABLE 15

Vehicle controlled percent Body Weight Change

| Dose minus control | Mean (percent) | Standard Error | Q-test (p-value) |
|---|---|---|---|
| 3 mg/kg – control | −4.65 | 1.09 | 0.34 (p = 0.56) |
| 10 mg/kg – control | −4.54 | 1.87 | 2.82 (p = 0.09) |

TABLE 16

Vehicle controlled percent Fat Mass Change

| Dose minus control | Mean (percent) | Standard Error | Q-test (p-value) |
|---|---|---|---|
| 3 mg/kg – control | −9.53 | 2.07 | 0.28 (p = 0.60) |
| 10 mg/kg – control | −8.41 | 2.16 | 0.23 (p = 0.63) |

TABLE 17

Vehicle controlled percent Food Intake Change

| Dose minus control | Mean (percent) | Standard Error | Q-test (p-value) |
|---|---|---|---|
| 3 mg/kg – control | −11.31 | 1.98 | 4.83 (p = 0.03) |
| 10 mg/kg – control | −8.43 | 2.31 | 0.08 (p = 0.77) |

The results demonstrate that N-[1-[[(4R)-5,6-dihydro-4H-imidazo[1,2-a][1]benzazepin-4-yl]carbamoyl]cyclopropyl]-4-ethoxy-benzamide (Examples 1, 3, 57) and 4-Chloro-N-[1-[[(4R)-5,6-dihydro-4H-imidazo[1,2-a][1]benzazepin-4-yl]carbamoyl]cyclopropyl]benzamide (Examples 2, 21, 58) reduce body weight, fat mass, and food intake in the diet-induced obese mouse model.

Formulation

Preparation of a formulation using hydroxypropyl methylcellulose acetate succinate (HPMC-AS-L), a grade that dissolves at pH 5.5 and that results in a 30% N-[1-[[(4R)-5,6-dihydro-4H-imidazo[1,2-a][1]benzazepin-4-yl]carbamoyl]cyclopropyl]-4-ethoxy-benzamide/70% HPMC-AS-L solid dispersion.

Film casting: Prepare sample using 350.12 mg of HPMC-AS-L, 150 mg of N-[1-[[(4R)-5,6-dihydro-4H-imidazo[1,2-a][1]benzazepin-4-yl]carbamoyl]cyclopropyl]-4-ethoxy-benzamide and 5 mL of 50/50 MeOH/Acetone solution as the solvent. Distribute portions of the solution among flat bottom Petri dishes that have been preheated to about 60° C. Store the films in a vacuum oven at 55° C. for 3.5 hours to remove all residual solvent.

Scrape the samples from the dish and reduce the particle size using a mortar and pestle. The HPMC polymers form an elastic film that, while easily removed, does not form a handleable powder making additional particle size reduction difficult. Grind samples with a mortar and pestle to form a uniform agglomerate size.

Spray dry using a GEA NERO SDMICRO™ spray drier: HPMC-AS-L (25.7 g); N-[1-[[(4R)-5,6-dihydro-4H-imidazo[1,2-a][1]benzazepin-4-yl]carbamoyl]cyclopropyl]-4-ethoxy-benzamide (11.0 g); atomization gas flow (~2.0 kg/h); outlet temperature during solvent flow (52° C.); and solution flow rate (~8 to 10 mL/min). Use a 70:30 mixture of acetone:methanol as the solvent. The mass flow of nitrogen to the system is 32.5 kg/h for each run. Each run uses a solution of about 4 weight % solids. A higher weight percent of solids may be used.

We claim:

1. A compound of the formula

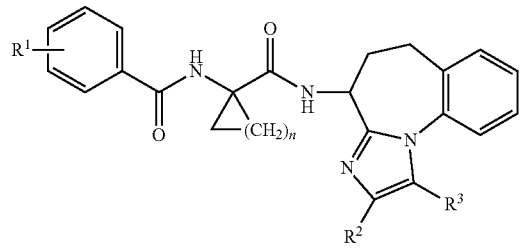

or a pharmaceutically acceptable salt thereof;
wherein
$R^1$ is selected from the group consisting of H, F, Cl, —$CF_3$, —$CH_3$, —OH, —O($C_1$-$C_4$ alkyl), —O-cyclopropyl, —O—$CH_2$-phenyl, —OC(H)$F_2$, and —$OCF_3$;
$R^2$ is selected from the group consisting of H and —$CH_3$;
$R^3$ is selected from the group consisting of H and —$CH_3$;
provided that at least one of the group consisting of $R^2$ and $R^3$ is H; and
n is 1, 2, or 3.

2. A compound or salt thereof as claimed by claim 1 wherein n is 1 or 3.

3. A compound or salt thereof as claimed by claim 2 wherein n is 1.

4. A compound or salt thereof as claimed by claim 2 wherein $R^3$ is H.

5. A compound or salt thereof as claimed by claim 4 wherein $R^2$ is H.

6. A compound or salt thereof as claimed by claim 5 wherein $R^1$ is selected from the group consisting of H, F, Cl, —CF$_3$, —CH$_3$, —OH, —OCH$_3$, —OCH$_2$CH$_3$, —OCH$_2$CH$_2$CH$_3$, —OCH$_2$CH(CH$_3$)$_2$, —O-cyclopropyl, —O—CH$_2$-phenyl, —OC(H)F$_2$, and —OCF$_3$.

7. A compound or salt thereof as claimed by claim 5 wherein R$^1$ is selected from the group consisting of Cl and —O—(C$_1$-C$_4$ alkyl).

8. A compound or salt thereof as claimed by claim 7 wherein R$^1$ is Cl.

9. A compound or salt thereof as claimed by claim 5 wherein Rl is —OCH$_2$CH$_3$.

10. A compound or salt thereof as claimed by claim 1 wherein the compound is the R isomer.

11. A salt as claimed by claim 10.

12. A compound of the formula

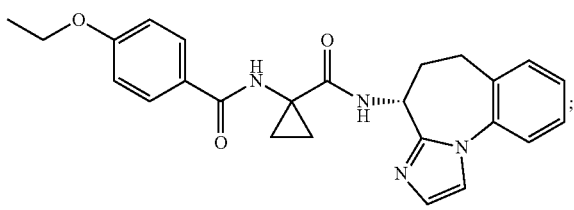

or a pharmaceutically acceptable salt thereof.

13. A compound of the formula:

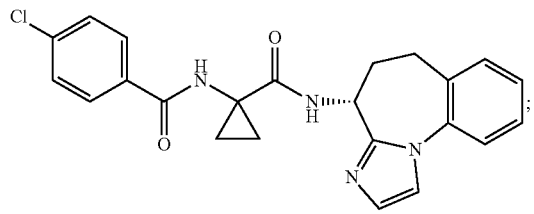

or a pharmaceutically acceptable salt thereof.

14. A pharmaceutical composition comprising a pharmaceutically acceptable and a compound as claimed by claim 1 or a pharmaceutically acceptable salt thereof.

15. A pharmaceutical composition as claimed by claim 14 further comprising a second pharmaceutical agent.

16. A method for treating obesity in a mammal, comprising the step of administering to the mammal a compound as claimed by claim 1 or a pharmaceutically acceptable salt thereof.

* * * * *

UNITED STATES PATENT AND TRADEMARK OFFICE
CERTIFICATE OF CORRECTION

PATENT NO. : 8,299,061 B2  
APPLICATION NO. : 12/961714  
DATED : October 30, 2012  
INVENTOR(S) : Brian Arnold Macklin et al.

Page 1 of 1

It is certified that error appears in the above-identified patent and that said Letters Patent is hereby corrected as shown below:

At Column 67, Line 10, in Claim 9, delete "Rl" and insert -- $R^1$ --, therefor.

At Column 68, Line 15, in Claim 14, line 2, after "acceptable" insert -- carrier --.

Signed and Sealed this  
Nineteenth Day of February, 2013

Teresa Stanek Rea  
*Acting Director of the United States Patent and Trademark Office*